(12) United States Patent
Gudas et al.

(10) Patent No.: US 6,706,506 B2
(45) Date of Patent: Mar. 16, 2004

(54) DETECTION OF EPITHELIAL CELL CANCERS AND PRECANCEROUS CONDITIONS

(75) Inventors: Lorraine J. Gudas, New York, NY (US); Xiaojio Guo, Branford, CT (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/911,343

(22) Filed: Jul. 23, 2001

(65) Prior Publication Data

US 2002/0055132 A1 May 9, 2002

Related U.S. Application Data

(60) Provisional application No. 60/220,222, filed on Jul. 24, 2000.

(51) Int. Cl.[7] .................... C12Q 1/68; G01N 33/48; C12N 9/00
(52) U.S. Cl. ............... 435/183; 436/64; 435/6
(58) Field of Search .................. 436/64; 435/6

(56) References Cited

PUBLICATIONS

Jurukovski et al (BioChim BioPhys Acta Jan. 4, 1999;1436(3):479–490).*

Zhan, HC et al., Differential Expression of the Enzyme Which Esterifies Retinol, Lecithin:Retinol Acyltransferase, In Substypes of Human Renal Cancer and Normal Kidney, Pending Publication in Clinical Cancer Research, submitted Feb. 6, 2003.

Blomhooff et al., J. Biol. Chem., 1985, 260:13560–13565.

Guo et al., Cancer Res., 1998, 58:166–176.

Chen et al., Cancer Res., 1997, 57:4642–4651.

Koller and Smithies, Proc. Natl. Acad. Sci. USA, 1989, 86:8932–8935.

Zijlstra et al., Nature, 1989, 342:435–438.

McLean et al., Clin. Chem., 1982, 28:693–696.

Ruiz et al., J. Biol. Chem., 1999, 274:3834–3841; and.

Huse et al., Science, 1989, 246:1275–1281.

* cited by examiner

Primary Examiner—Anthony C. Caputa
Assistant Examiner—Christopher Yaen
(74) Attorney, Agent, or Firm—Darby & Darby

(57) ABSTRACT

Epithelial cell cancers and precancerous conditions are detected by assaying for LRAT expression. Failure to detect LRAT expression indicates presence of cancer, and detection of lower than normal level of LRAT expression indicates a precancerous condition.

14 Claims, 10 Drawing Sheets

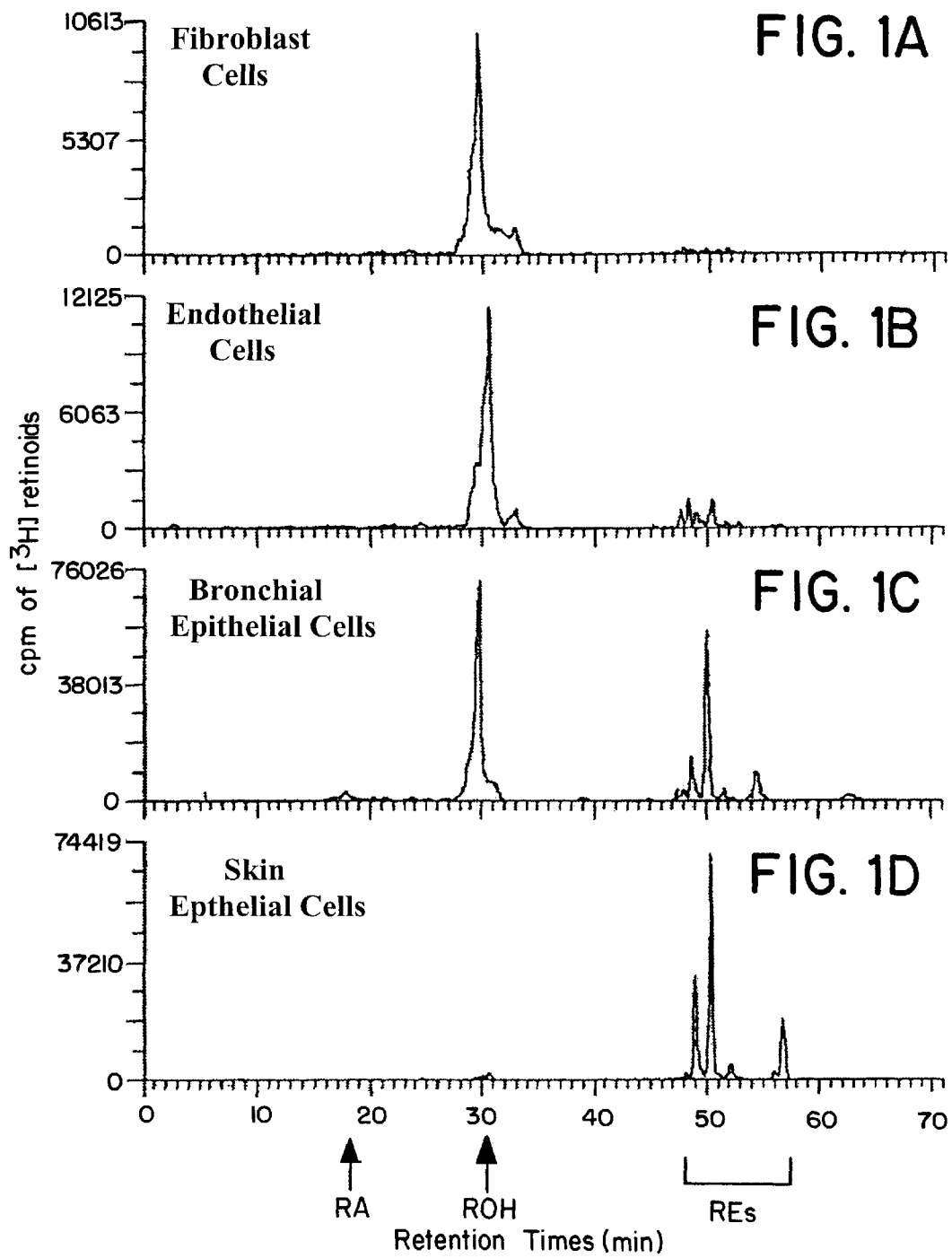

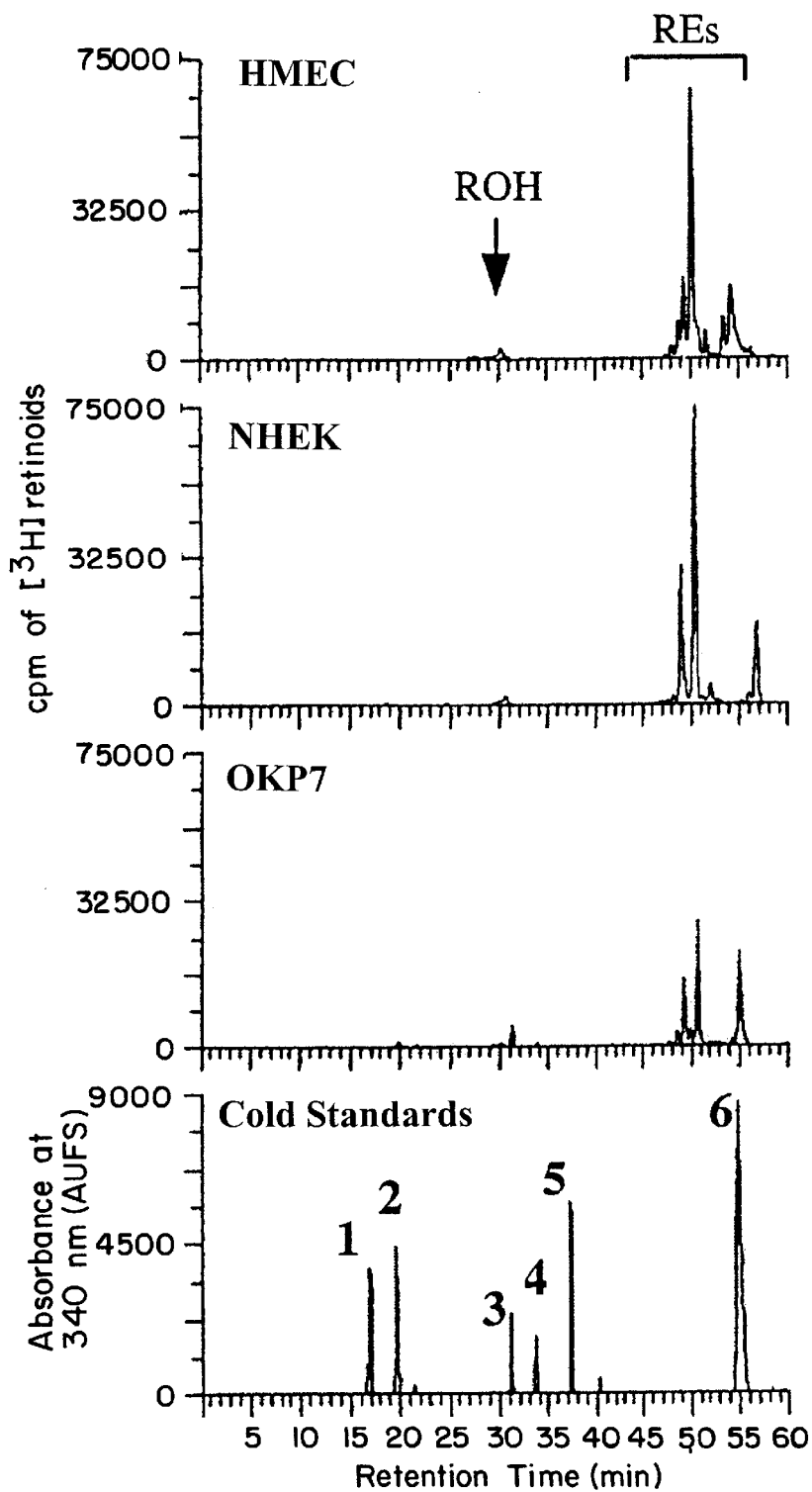

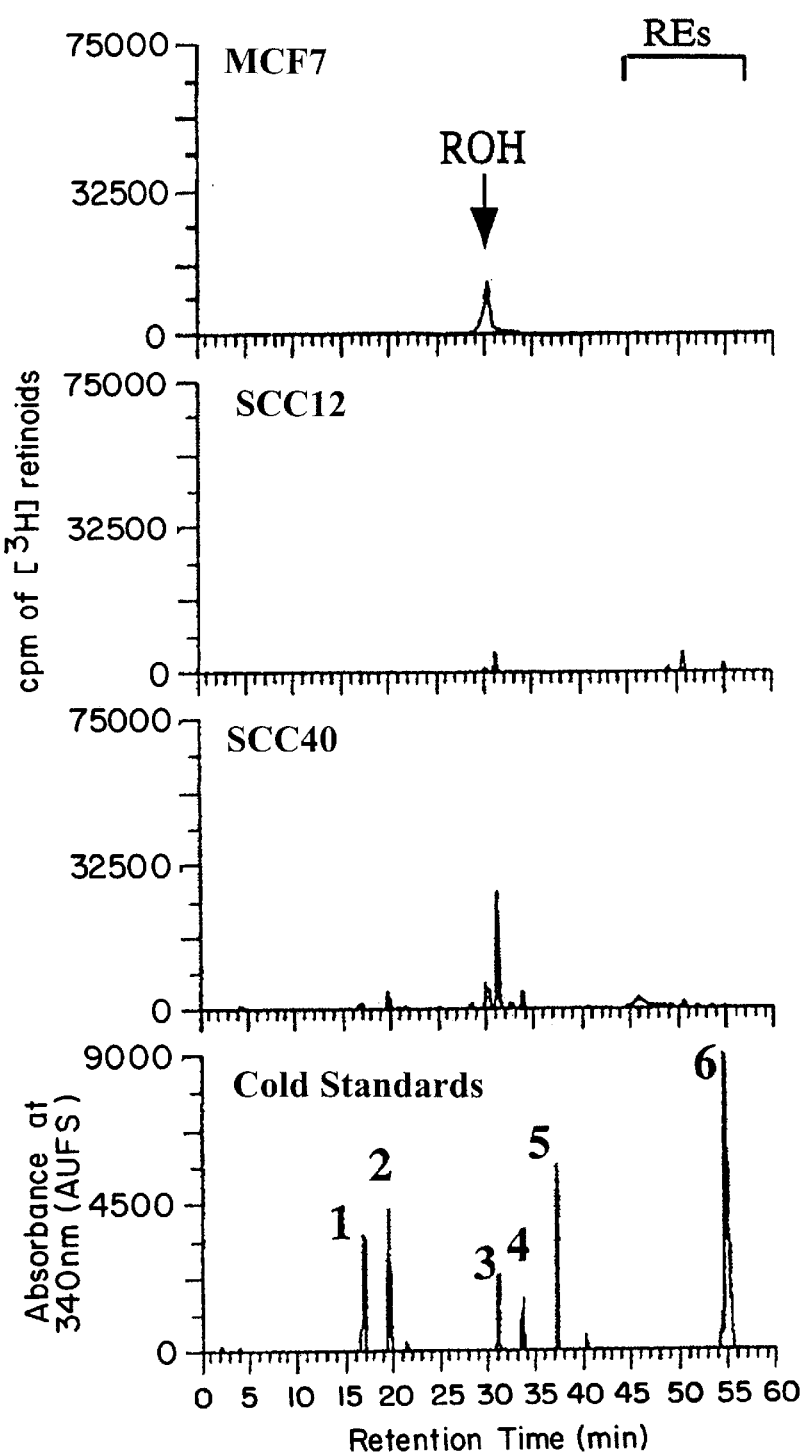

DETECTION OF EPITHELIAL CELL CANCERS AND PRECANCEROUS CONDITIONS

This application claims priority under 35 U.S.C. §119(e) of provisional application Ser. No. 60/220,222, filed Jul. 24, 2000, which is incorporated herein by reference in its entirety.

This invention was made at least in part with United States Government support under National Institutes of Health grants R01DE10389, R01EY04096, R01EY00444, and R01EY00331. The United States Government has certain rights in the invention.

FIELD OF THE INVENTION

The invention is directed to a method of determining the presence or absence of cancer or a precancerous condition in epithelial cells, i.e., epithelial cell carcinomas or precancerous epithelium.

BACKGROUND OF THE INVENTION

Retinoids

Retinoids (vitamin A and its metabolites) can act as chemopreventive and/or chemotherapeutic agents for several types of cancer (Bertram et al., Cancer Res. 1987, 47:3012–3031.; Moon et al., In Sporn, M. B., Roberts, A. B. and Goodman, D. S. (ed.) *The Retinoids: Biology, Chemistry and Medicine*, 1994, Raven Press, New York, pp. 573–596; Hong et al. In Sporn, M. B., Roberts, A. B. and Goodman, D. S. (ed.) *The Retinoids: Biology, Chemistry, and Medicine*, 1994, Raven Press, New York, pp. 597–630; Hong et al., Science 1997, 278:1073–1077. Retinoids exert major effects on the growth and differentiation of normal, premalignant, and malignant epithelial cells both in vitro and in vivo (Gudas et al., In Sporn, M. B., Roberts, A. B. and Goodman, D. S. (ed.) *The Retinoids: Biology, Chemistry, and Medicine*, 1994, Raven Press, New York, pp. 443–520). Retinol can be metabolized to retinyl esters and to various structurally related compounds, such as retinoic acid (RA), retinaldehyde, 4-oxoretinol, 14-hydroxy-4-14-retroretinol (14-HRR), and anhydroretinol in many cell types (Blaner et al., In Sporn, M. B., Roberts, A. B. and Goodman, D. S. (ed.) *The Retinoids: Biology, Chemistry, and Medicine*, 1994, Raven Press, New York, pp. 229–256; Kurlandsky et al., J. Biol. Chem. 1994, 269:32821–32827; Achkar et al., Proc. Natl. Acad. Sci. USA 1996, 93:4879–4884; Lane et al., Proc. Natl. Acad. Sci. USA 1999, 96:13524–13529; Buck et al., Science 1991, 254:1654–1656; Buck et al, J. Exp. Med. 1993, 178:675–680). While retinoic acid in particular has been demonstrated by many researchers to be useful in the prevention and treatment of cancer in humans (Hong et al., Retinoids in Oncology 1993, Marcel Dekker, New York; Warrell Jr., et al., N. Engl. J. Med 1991, 324:1385–1393), more recently other retinoids such as anhydroretinol have been shown to prevent cancer in animal models (Shealy et al., Oncol. Rep. 1998, 5:857–860).

Retinyl esters are the major metabolites of retinol in some normal cells and tissues, whereas there are data that other cell types are not capable of esterifying retinol. For example, human keratinocytes (Randolph et al. J. Biol. Chem. 1993, 268:9198–9205; Törmä et al., J. Invest. Dermatol. 1990, 94:132–138; Kurlandsky et al., J. Biol. Chem. 1996, 271:15346–15352; Guo et al., Cancer Res. 1998, 58:166–176; Creek et al. J. Nutr. 1993, 123:356–361; Randolph et al. J. Invest. Dermatol. 1996, 106:168–175), human intestinal Caco-2 cells (Quick et al, Biochemistry 1990, 29:11116–11123.) cultured tracheal epithelial cells (Bhat et al., Biochim. Biophys. Acta 1987, 922:18–27), retinal pigment epithelial cells (Das et al., Biochem J. 1988, 259:459–465; Barry et al., J. Biol. Chem. 1989, 264:9231–9238; Saari et al., J. Biol. Chem. 1989, 264:8636–8640), liver (Ong et al., J. Biol. Chem. 1988, 263:5789–5796; Yost et al., J. Biol. Chem. 1988, 263:18693–18701; Blomhoff et al., J. Biol. Chem. 1985, 260:13560–13565; Matsuura et al., J. Nutr. 1997, 127:218–224; Shimada et al. Arch. Biochem. Biophys. 1997, 344:220–227), and mammary epithelial cells (Ross et al., J. Lipid Res. 1982, 23:133–144; Bhat et al., Cancer Res. 1989, 49:139–144; Chen et al. Cancer Res. 1997, 57:4642–4651) exhibit a high level of retinol esterification activity. Two enzyme activities can catalyze retinyl ester synthesis: acyl CoA:retinol acyltransferase (ARAT) and lecithin:retinol acyltransferase (LRAT). The enzyme activities can be distinguished from each other by substrate preferences and differential sensitivities to various inhibitors (Ong et al., J. Biol. Chem. 1988, 263:5789–5796; Yost et al., J. Biol. Chem. 1988, 263:18693–18701; Herr et al. J. Nutr. Biochem. 1991, 503–511). LRAT employs the acyl group at the sn1 position of membrane phospholipid (Herr et al. J. Nutr. Biochem. 1991, 503–511) as an acyl donor, whereas ARAT utilizes acyl CoA (Ross et al., Methods Enzymol. 1990, 189:442–445). ARAT catalyzes esterification of free retinol (Ong et al., J. Biol. Chem. 1988, 263:5789–5796; Yost et al., J. Biol. Chem. 1988, 263:18693–18701; Herr et al. J. Nutr. Biochem. 1991, 503–511; Ong, et al., Nutr. Rev. 1994, 52:S24–S31), while LRAT can utilize both free retinol and retinol bound to the cellular retinol binding protein I as a substrate (Saari et al., Vision Res. 1984, 24:1595–1603). However, it was shown that elevation of the cellular retinol binding protein (CRBP-I) did not enhance retinyl ester storage in transgenic animals (Troen et al., J. Nutr. 1996, 126:2709–2719). An LRAT partial cDNA was recently cloned from human retinal pigment epithelium cells. This cDNA hybridizes to a major RNA transcript of approximately 5.0 kb and minor transcripts of 2.2.–2.5 kb in several tissues, including the testis and liver (Ruiz, et al., J. Biol. Chem. 1999, 274:3834–3841). The ARAT gene has not yet been cloned.

The hydrolysis of retinyl esters also can occur in hepatic cells and in other types of epithelial cells (Cooper, et al, J. Nutr. 1987, 117:2066–2071; Blaner, et al., FEBS Lett. 1990, 274: 89–92; Harrison et al., J. Biol. Chem. 1989, 264:17142–14147; Ghosh, et al. Lipids 1990, 25:221–225; Ritter et al., Biochim. Biophys. Acta 1996, 1291: 228–236; Schlinder, et al, Eur. J. Biochem. 1998, 251:863–873.) Recently, a neutral, bile salt-independent retinyl ester hydrolase (NREH) was purified (Sun, et al. ES-2. J. Biol. Chem. 1997, 272:24488–24493), and a hepatic, bile salt dependent retinyl ester hydrolase was cloned and shown to be identical to pancreatic carboxylester lipase (Chen et al., Proc. Soc. Exp. Biol. Med. 1997, 215:186–191). The retinyl ester hydrolase(s) which are responsible for retinyl ester hydrolysis in many extra-hepatic tissues have not been well characterized, though retinyl ester hydrolases have been described in tissues and cell types in addition to liver. In the retinal pigment epithelium (RPE), all-trans retinyl esters are substrates for an isomerohydrolase which converts the esters into 11-cis retinol; 11-cis retinol is then oxidized and converted to 11-cis retinaldehyde, the chromophore for rhodopsin and cone pigments (Bernstein et al., Proc. Natl. Acad. Sci. USA 1987, 84:1849–1853; Deigner et al., Science 1989, 244:968–971). In adipocytes, there is evidence that retinyl esters can be hydrolyzed by a cyclic AMP dependent enzyme-like hormone sensitive lipase (Wei et al., J. Biol. Chem. 1997, 272:14159–14165).

In contrast to normal epithelial cells, there are some reports that in normal human fibroblasts retinol, although readily taken up by the fibroblasts, is not metabolized to either retinoic acid or retinyl esters (Rundhaug et al., Cancer Res. 1987, 47:5637–5643; Randolph et al., J. Invest. Dermatol. 1998, 111:478–484). In another study, it was reported that cultured human dermal fibroblasts, treated with retinol, metabolized retinol to retinoic acid and retinyl esters (Bailly et al., Exp. Dermatol. 1998, 7:27–34). Little information is available concerning retinol metabolism in normal human endothelial cells. It was previously reported that isolated endothelial cells from the liver contained very low levels of retinoids (Blomhoff et al., J. Biol. Chem. 1985, 260:13560–13565). However, retinoids can influence endothelial cell growth, gene expression, and morphology (Braunhut et al., Microvasc. Res. 1991, 41:47–62; Kooistra et al., J. Biochem. 1995, 232:425–432; Braunhut et al., J. Biol. Chem. 1994, 269:13472–13479; Spencer-Green et al., Clin. Immunol. Immunopath. 1994, 72:53–61; Thompson et al., Eur. J. Biochem. 1991, 203:627–632).

While the functions of retinyl esters are not fully understood, it is believed that retinyl esters act as a storage form for retinol both in the liver and in many other tissues in the body. Interestingly, carcinoma cells of the breast, oral cavity, and skin are deficient in the esterification of retinol (Guo et al., Cancer Res. 1998, 58:166–176; Chen et al. Cancer Res. 1997, 57:4642–4651). These recent data, together with the aforementioned data, suggest that the lack of retinyl esters in carcinoma cells may be associated with or even contribute to their tumorigenic phenotype (Guo et al., supra, Chen et al., supra). However, there is no indication of how this deficiency occurs, or how it could be corrected.

Carcinomas

Cancers or malignant tumors are classified according to the type of tissue from which they originate. The broadest division of cancers separates the carcinomas, tumors which arise from epithelial tissues, and the sarcomas, which arise from all other tissues. Epithelium is tissue that covers the internal or external surfaces of the body. Thus, skin, the lining of the mouth, stomach, intestines, bladder and so on are all epithelial tissue.

Within the category of carcinomas, there are many subdivisions, corresponding to the types of different epithelium from which they may be derived. Therefore, the skin, which consists of a type of epithelium called squamous epithelium, can give rise to squamous cell carcinomas. There are other epithelial cells also present in the skin, basal cells, which give rise to basal cell carcinomas, and melanocytes, which give rise to melanomas.

Adenocarcinoma is a cancer originating in glandular cells. Adenocarcinomas occur in the lungs, from small glands in the bronchi; in the stomach from one of the several types of glands lining it; and in the colon, breast, ovaries, testes, prostate and in other locations. Adenocarcinomas arising from different organs can often be identified by the pathologist microscopically, even when they are removed from a different location where they may have metastasized, such as the liver. Thus, it is common to refer to an adenocarcinoma of the stomach which has metastasized to the liver, or one from the colon metastasized to the lungs.

Adenocarcinomas are the most common cell type of cancer, since they include almost all breast cancers, all colon cancers, all prostate cancers, and a fair percentage of lung cancers. The cause of most adenocarcinomas is still unknown, and is the subject of intensive research. Various studies have reported associations of certain carcinomas with other factors such as the association of early menstruation with carcinoma of the breast, or lack of fiber associated with colon cancer. However, these reports change as with fiber and colon cancer (no association) or identify associations that are difficult or impossible change.

Presently, detection of epithelial cell carcinomas involves a pathologist observing cells under a microscope to consider morphology and making a subjective judgment as to whether cancer is present. Thus, there remains a need in the art for objective, accurate methods to determine whether or not an epithelial cell is cancerous or predisposed to become transformed (precancerous condition). The present invention addresses this and other needs in the art.

SUMMARY OF THE INVENTION

The instant invention advantageously replaces or supplements the subjective judgment that is now conventional in the diagnosis of hyperplastic, particularly cancerous, conditions with an objective test and minimizes the need for human judgment.

The instant invention is directed to an assay for determining the presence or absence of cancer or the presence of precancerous condition in epithelial cells, and is useful for detecting epithelial cell carcinomas including colon, renal, prostate, oral cavity, lung, breast and skin carcinomas and precancerous conditions associated therewith.

In one embodiment, the invention provides a kit for determining the presence or absence of a cancer or precancerous condition in epithelial cells, which kit comprises an assay for detection of expression levels of LRAT. One preferred LRAT detection assay comprised within the kit is a radiolabeled retinol and an unlabeled retinol, which are used to measure expression levels base on LRAT's enzymatic activity. Another preferred LRAT detection assay comprised within the kit is a labeled nucleic acid probe or primer that specifically hybridizes to LRAT mRNA, thereby detecting expression of mRNA that is translated into a functional LRAT protein. Yet another preferred LRAT detection assay comprised within the kit is an antibody that specifically binds to LRAT protein in epithelial cells.

In another aspect, the invention provides a method for treating cancer of an epithelial cell or preventing transformation of a precancerous epithelial cell, which method comprises activating LRAT protein expression in the epithelial cell. In a preferred embodiment, LRAT expression is activated by introducing a gene encoding LRAT into the cell.

The invention also provides an expression vector for expression in humans, which vector encodes LRAT under control of an expression control sequence that provides for expression in epithelial cells. In a preferred embodiment, the vector is administered in vivo as an appropriate pharmaceutical composition, where it enters the cells of the organism and mediates expression of the construct.

In its preferred aspect, the invention comprises determining the amount of lecithin:retinol acyltransferase (LRAT) protein present in the cells being tested. Failure to detect LRAT protein indicates presence of cancer, and detection of a lower than normal level of LRAT protein indicates a precancerous condition. It has been discovered that normal epithelial cells contain retinyl esters, whereas cancerous epithelial cells do not, and that this is associated with the presence of LRAT protein in normal epithelial cells but not in cancerous epithelial cells. Abundant levels of LRAT expression are detectable in normal epithelial cells, but LRAT expression is not detected by Western Blot analysis of, or immunohistochemistry studies on, epithelial cells from epithelial cell carcinomas, and intermediate levels of LRAT expression are detected by Western Blot analysis or immunohistochemistry in cells from benign hypertrophy (precancer) epithelial tissues.

These and other aspects of the invention are described in greater detail in the Examples, including Drawings, and Detailed Description, infra.

DESCRIPTION OF THE DRAWINGS

FIGS. 1A, 1B, 1C and 1D. Metabolism of [$^3$H]Retinol in various types of normal cells. HPLC tracings of GMPO970, a human normal fibroblast cell strain, panel A; a primary culture of human umbilical vein endothelial cells (HUVEC), panel B; a normal human bronchial epithelial cell strain (NHBE), panel C; and a normal human epidermal keratinocyte cell strain (NHEK), panel D. Cells were cultured in the presence of [$^3$H]retinol for varying times; the data shown are for 15 h. Cells and one-fourth of the medium were harvested, and retinoids were extracted and separated by reverse phase HPLC analysis as described in the Materials and Methods (Example 1). Only the intracellular retinoids are shown. Nonradiolabeled retinoids were included with each sample as standards to determine the elution times of the various retinoids. Arrows indicate the elution positions of [$^3$H]retinoic acid (RA, 18 min) and [$^3$H]retinol (ROH, 29.8 min), and a bracket indicates the [$^3$H]retinyl esters at 48–57 min, respectively. Note that the y axes are different in the four panels; the cell numbers are $1.3 \times 10^6$ cells, GM0970; $1.2 \times 10^6$ cells, HUVEC; $1.0 \times 10^6$ cells, HNBE; and $9.7 \times 10^6$ cells, NHEK. This experiment was performed three times with very similar results. Data from one experiment are shown here.

FIGS. 2A–2H. Metabolism of [$^3$H]Retinol in Normal Human Epithelial Cell Strains and in Human Carcinoma Lines. Normal cell strains are A) human mammary epithelial cells (HMEC); B) normal human epidermal keratinocytes (NHEK); C) oral cavity keratinocytes, strain OKP-7 from the soft palate. Tumor lines are E) MCF-7 breast carcinoma cells; F) SCC-12, a squamous carcinoma cell line from the skin; G) SCC-40, a squamous cell carcinoma line from a tumor in the soft palate. Nonradiolabeled standards are shown in panels D and H; 1, all-trans-4-oxoretinol; 2, all-trans retinoic acid; 3, all-trans retinol; 4, all-trans retinaldehyde; 5, all-trans retinyl acetate; 6, retinyl palmitate. Cells were labeled for 22 h with 50 nM [$^3$H]retinol. Cells and one-fourth of the medium were harvested, and retinoids were extracted and separated by reverse phase HPLC analysis. Only the intracellular retinoids are shown. Nonradiolabeled retinoids were included with each sample as standards to determine the elution times of the various retinoids. The data for each sample are plotted as [$^3$H] counts per minute vs. time. The peaks that correspond to [$^3$H]retinol and [$^3$H]retinyl esters are at 30.5 min and 47–56 min, respectively. This experiment was performed three times with very similar results. One representative HPLC tracing for each cell line is shown here.

DETAILED DESCRIPTION

Figure 3A:
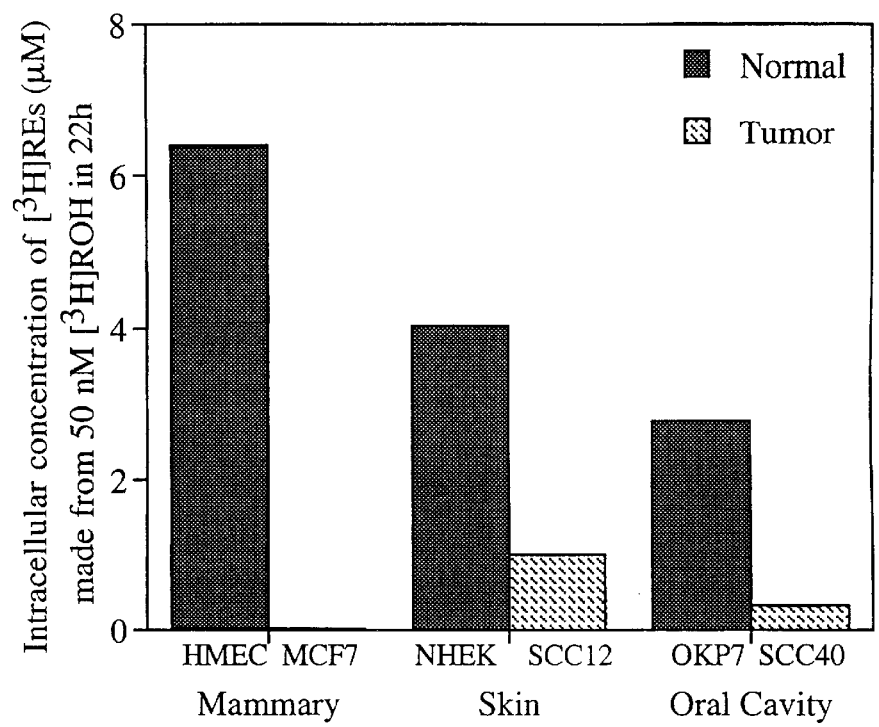
FIGS. 3A and 3B. The data from FIGS. 2A, 2B, 2C, 2E, 2F and 2G are shown in a quantitative format in panels A and B. Panel 3A shows the intracellular [$^3$H]retinyl ester levels normalized to $1 \times 10^6$ cells. Panel 3B shows the total (intracellular plus in the medium) [$^3$H]retinol remaining at 22 h, calculated as described in the material and methods.

The present invention advantageously provides a method for objectively identifying the cancer state of epithelial cells.

The term "cancer state" refers to whether the epithelial cell is a normal (untransformed) epithelial cell, has developed a precancerous vena type, or has transformed into a cancerous epithelial cell (carcinoma). The ability to objectively identify these different cancer states provide the great advantage to pathologists, and in turn to oncologists charged with treating epithelial cell hyperplasias. In particular, identification of carcinoma demands more aggressive therapy, including chemotherapy, radiation, surgery resection, immunotherapy, or gene therapy, than identification of a precancerous condition would require.

The present invention is based, in part, on observations concerning deficiencies of retinol esterification in epithelial cancer cells compared to normal epithelial cells. When exogenous [$^3$H]retinol (vitamin A) is added to the culture medium, normal human epithelial cells from the oral cavity, skin, lung, and breast take up and esterify essentially all of the [$^3$H]retinol within a few hours. As shown by [$^3$H]retinol pulse-chase experiments, the normal epithelial cells then slowly hydrolyze the [$^3$H]retinyl esters to [$^3$H]retinol, some of which is then oxidized to [$^3$H]retinoic acid (RA) over a period of several days. In contrast, cultured normal human fibroblasts and human umbilical vein endothelial cells (HUVEC) do not esterify significant amounts of [$^3$H]retinol, and the lack of [$^3$H]retinol esterification is correlated with the lack of expression of LRAT (lecithin:retinol acyltransferase) transcripts in the normal fibroblast and HUVEC strains. These results indicate that there are differences in the ability to esterify retinol among various normal, differentiated cell types.

It has now been discovered that human carcinoma cells (neoplastically transformed epithelial cells) of the oral cavity, skin, breast, and other epithelial tissues, do not esterify much [$^3$H]retinol. More significantly, this lack of [$^3$H]retinol esterification in the carcinoma cells is surprisingly associated with greatly reduced expression of the active LRAT protein. These experiments suggest that a retinoid deficient state in the tumor cells could develop because of the lack of retinyl esters, a storage form of retinol, which in turn is due to deficient LRAT activity. These observations advantageously provide an objective strategy for evaluating the cancer state of epithelial cells. Such an approach was not predictable, since HUVEC and normal fibroblast strains also lack LRAT activity.

Transcripts for the neutral, bile salt-independent retinyl ester hydrolase and the bile salt-dependent retinyl ester hydrolase were undetectable in all of the normal cell types, including the epithelial cells.

Together, these discoveries establish a new, objective paradigm for detecting the cancer state of epithelial cells: normal LRAT activity indicates that the cells are normal; very low or no LRAT activity indicates that the cells are cancerous; and a lower than normal level activity indicates a precancerous condition.

Abbreviations used herein include the following: AHD-2, aldehyde dehydrogenase-2; ALDH-1, aldehyde dehydrogenase-1; ARAT, acyl CoA:retinol acyltransferase; DME, Dulbecco's modified Eagles medium; HMEC, normal human mammary epithelial cells; HPLC, high performance liquid chromatography; HUVEC, human umbilical vein endothelial cells; LRAT, lecithin:retinol acyltransferase; HNBE, normal human bronchial epithelial cells; NHEK, normal human epidermal keratinocytes; NREH, neutral retinyl ester hydrolase; PBS, phosphate buffered saline; RA, all-trans retinoic acid; RALDH-2, retinaldehyde dehydrogenase-2; REH, retinyl ester hydrolase; ROH, all-trans retinol; RPE, retinal pigment epithelium; SCC, squamous cell carcinoma.

The terms "epithelial cell" and "epithelial cell cancer" (i.e., carcinoma) have their ordinary meanings, e.g, as set forth in the Background. A "precancerous condition" also has its ordinary meaning, i.e., an unregulated growth without metastasis, and includes various forms of hyperplasia and benign hypertrophy. For example, an epithelial cells can be a prostate gland cell. Benign hyperplasia of the prostate is a well known condition, particularly in older men, that leads to difficulties with bladder control. Prostate adenocarcinoma is an important, occasionally aggressive, and frequently fatal disease in men. As noted above, the present invention permits one to objectively distinguish all three states in prostate cells.

As used herein, the term "presence" of cancer means that the cell has become transformed and exhibits a cancerous phenotype, which is detected herein by the absence of LRAT expression. The presence of a precancerous condition means that the cell shows a hyperplastic phenotype, which is demonstrated herein by a reduced level of LRAT expression. A hyperplastic cell has a greater predisposition to become cancerous. Thus, the "absence" of cancer means that the cell has not become transformed, and the absence of a precancerous condition means that the cell has not become hyperplastic. The absence of these conditions id demonstrated herein by a normal level of LRAT expression. A cell's cancer state then refers to whether it demonstrates the presence or absence of cancer or a precancerous condition.

The term "expression of active LRAT" refers to expression of a functional LRAT protein. A functional LRAT protein catalyzes the esterification of retinols. As set forth below, the invention provides multiple approaches to detecting the level of active LRAT expression, including biochemically (by detecting LRAT's enzymatic activity), by detecting expression of mRNA that is translated into a functional LRAT versus mRNA that is not translated into a functional LRAT, and quantifying LRAT protein, e.g., by immunoassay or direct biochemical detection.

The term "vector for expression in humans in vivo" as used herein means that the vector at least includes an expression control sequence (e.g., a promoter or minimal promoter with regulatory sequences and/or an enhancer) that is effective in human epithelial cells, and preferably that the vector is safe and effective in humans. Such a vector will, for example, omit extraneous genes not involved in developing immunity. If it is a viral vector, it will omit regions that permit replication and development of a robust infection, and will be engineered to avoid development of replication competence in vivo. Such vectors are preferably safe for use in humans; in a more preferred embodiment, the vector is approved by a government regulatory agency (such as the Food and Drug Administration) for clinical testing or use in humans. Specific vectors are described in greater detail below.

A "subject" is preferably a human, but can be a non-human animal, preferably a mammal, and more preferably still a domesticated mammal, such as a dog or cat.

The term "about" or "approximately" means within an acceptable error range for the particular value, which will depend on how the value is measured or determined. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Diagnostics

As used herein, the term "diagnosis" refers to the identification of the disease at any stage of its development, i.e., the cancer state of the cell, and also includes the determination of a predisposition of a subject to develop the disease. An early diagnosis is preferred, preferably in a subject that has not shown any symptoms of carcinoma yet. Subjects with a higher risk of developing the disease, e.g., with a family history of carcinoma such as, but not limited to, colorectal, breast, ovarian, and prostate carcinomas, are of particular concern.

As noted above, the method of the invention comprises assessing the level of expression or activity of LRAT in epithelial cells of a test subject and comparing it to the normal level of expression of active LRAT. A "normal level" is a level in a normal epithelial cell from the same subject, the same epithelial tissue at an earlier time, or a level established for a general population. An decrease of expression or activity of LRAT in the test subject compared to the normal control is indicative of a precancerous condition or carcinoma in the test subject. "Failure to detect LRAT expression" means that the level of expression of active LRAT is at or below the ability to detect such expression by whatever means are employed, e.g., as set forth below. A "lower than normal" level means that the level of active LRAT is below the acceptable variation of the normal level for the particular method of measurement.

The diagnostic methods of the invention may preferably be performed in vitro, in a biological sample of a test subject, that is compared to a control sample. In particular, one can determine the level of expression of LRAT in biopsy or tumor resection samples from a subject.

A "biological sample" is any body tissue or fluid likely to contain an epithelial cell in which one can determine expression of LRAT, e.g., the level of LRAT protein or mRNA. Such samples preferably include biopsy samples, e.g., breast, colon polyp, cervical, prostatic, and other tissue biopsies, particularly needle biopsies; resected tumor samples; and, where metastasis is suspected, individual cells from blood, urine, semen, vaginal secretions, lung secretions or lavage, and similar body fluids. As noted above, biochemical (enzymatic acitivty), nucleic acid based, and protein based assays permit detection of the level of LRAT expression.

Biochemical Assays

In one embodiment, one can detect the level of LRAT activity by measuring its enzymatic activity, e.g., the rate of retinol metabolism, and particularly retinol esterification, in epithelial cells.

One method to measure retinol esterification employs the following technique (all retinoid solutions and samples are handled under red or dim light to prevent photodegradation). Cells are plated, e.g., at $1\times10^6$ cells per 60 mm dish, 24 h prior to addition of a radiolabeled retinol, preferably [$^3$H] retinol. Cells are washed prior to labeling and cultured for various periods in labeling medium containing an appropriate concentration, e.g., 50 nM, labeled retinol. A separate control consisting of labeling medium without cells is preferably included during the incubation period. Cells and a portion of media are collected. Cells are washed and removed. They can be stored at −70° C. until retinoid extraction. Cell numbers are counted from parallel dishes from each treatment at the time of cell harvest.

For pulse chase experiments, the cells are cultured with labeled retinol for a defined period, e.g., 24 hours. After incubation, the cells are rinsed and then incubated in growth medium without labeled retinol for an additional one to eight days. At various times following the removal of labeled retinol from the medium, dishes of cells are harvested and retinoids extracted and subjected to HPLC analysis.

Retinoids can be extracted as described (McLean et al., Clin. Chem. 1982, 28:693–6). Non-radiolabeled retinoid standards can be added to the samples prior to extraction. For example, 350 μl acetonitrile/butanol (50:50, v/v), 0.1% butylated hydroxytoluene (BHT) are added to 0.5 ml of cells or medium samples. The mixtures are vortexed thoroughly for 30 sec. After addition of 300 μl of a saturated (1.3 kg/liter) $K_2HPO_4$ solution and thorough mixing, the samples are centrifuged for 10 min at 3000×g. The upper organic layer is collected and transferred to an injector vial for automated HPLC analysis, e.g., as described in the examples.

Retinoids are preferably identified by HPLC based on at least two criteria: an exact match of the retention times of unknown peaks with those of authentic retinoid standards and identical UV spectra (220–400 nm) of unknowns against spectra from authentic retinoid standards during HPLC by the use of the photodiode array detector. RA can also be identified by the shift of the retention time of the methylated RA derivative to the same position as the corresponding methyl ester of the RA standard.

Nucleic Acid Based Assays

In one embodiment, the determination of the level of expression of LRAT encompasses the use of nucleic acid sequences such as specific oligonucleotides to detect the presence of differentially spliced mRNA that encodes LRAT nucleic acid in a biological sample. In particular, as shown in the examples, detection of 5 kb (kilobase) and 2.5 kb mRNA species along with a 3 kb species demonstrates expression of active LRAT as defined herein, while detection of only 3 kb and 1.5 kb species evidences non-expression (i.e., failure to detect expression) of active LRAT, and a mixture of 5 kb, 2.5 kb, and 1.5 kb species with the 3 kb species indicates intermediate expression.

For that purpose, one skilled in the art may use hybridization probes in solution hybridizations and in embodiments employing solid-phase procedures. In embodiments involving solid-phase procedures, the test or probe nucleic acid is adsorbed or otherwise affixed to a selected matrix or surface. The fixed, single-stranded nucleic acid is then subjected to specific hybridization with selected probes or with samples. For example, one may use the well known nucleic acid based microarrays, in which probe nucleic acids are immobilized, to detect the different LRAT mRNA species (see for example the following: U.S. Pat. Nos. 6,045, 996; 6,040,138; 6,027,880; 6,020,135; 5,968,740; 5,959, 098; 5,945,334; 5,885,837; 5,874,219; 5,861,242; 5,843, 655; 5,837,832; 5,677,195 and 5,593,839).

In another embodiment, one skilled in the art may use oligonucleotide primers in an amplification technique, such as a RT-PCR ("reverse transcriptase-polymerase chain reaction"), to specifically amplify the target mRNA potentially present in the biological sample.

As used herein, the term "oligonucleotide" refers to a nucleic acid, generally of at least 10, preferably at least 15, and more preferably at least 20 nucleotides, preferably no more than 100 nucleotides, that is hybridizable to an mRNA molecule that encodes LRAT gene. Oligonucleotides can be labeled, e.g., with $^{32}P$-nucleotides or nucleotides to which a label, such as biotin, has been covalently conjugated. Generally, oligonucleotides are prepared synthetically, preferably on a nucleic acid synthesizer. As set forth in the patents noted above, for nucleic acid arrays oligonucleotides can be synthesized in situ. Accordingly, oligonucleotides can be prepared with non-naturally occurring phosphoester analog bonds, such as thioester bonds, etc.

Protein Based Assays

As an alternative to analyzing LRAT nucleic acids, one can evaluate LRAT on the basis of protein expression. In a preferred embodiment, LRAT is detected by immunoassay. For example, Western blotting and immunohistochemistry both permit detection of the presence or absence of LRAT. Other immunoassay formats can also be used in place of Western blotting, as described below for the production of antibodies.

For the detections, rabbit polyconal antiserum against a mixture of two LRAT peptides is useful, for example. Obtaining this antiserum is described in Ruiz., et al., J. Biol. Chem. 1999, 274:3834–3841.

A procedure for assaying for LRAT expression by Western Blot analysis is described in Ruiz, et al., supra. Briefly, polyclonal antisera is generated in rabbits to a mixture of two different human LRAT peptides. Total cells protein is used, and blot analysis on nitrocellulose fibers is performed using antiserum diluted to $\frac{1}{1,000}$ for detection of LRAT. Protein bands can be detected by the ECL system (Pierce, Rockford, Ill.).

A procedure for evaluating for LRAT expression in tissue is as follows: Polyclonal antibody for human LRAT is isolated from rabbits. Staining is performed using the polyclonal antibody (1:250) and standard immunoperoxidase methods. A biotinylated secondary antibody against rabbit is localized with streptavidin biotin conjugated to peroxidase and final color reaction is developed with a diaminobenzideine substrate (Vector Laboratories, Burlingame, Calif.).

In ELISA assays, an anti-LRAT antibody is immobilized onto a selected surface, for example, a surface capable of binding proteins such as the wells of a polystyrene microliter plate. After washing to remove incompletely adsorbed polypeptides, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface. The immobilizing surface is then contacted with a sample, such as clinical or biological materials, to be tested in a manner conductive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or borate buffer. Following formation of specific immunocomplexes between the test sample and the bound polypeptide, and subsequent washing, the occurrence, and an even amount of immunocomplex formation may be determined by subjecting the immunocomplex to a second antibody having specificity for LRAT. To provide for detection, the second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

Other ELISA and soluble immunoassay variations include competition assays and release assays (see, e.g., U.S. Pat. Nos. 5,710,009; 3,817,834; 4,318,707; and 4,434,236).

Alternatively, a biochemical assay can be used to detect expression of LRAT, e.g., by the presence or absence of a band by polyacrylamide gel electrophoresis; by the presence or absence of a chromatographic peak by any of the various methods of high performance liquid chromatography, including reverse phase, ion exchange, and gel permeation; by the presence or absence of LRAT in analytical capillary electrophoresis chromatography, or any other quantitative or qualitative biochemical technique known in the art.

The components for detecting LRAT protein can be conveniently provided in a kit form. In its simplest embodiment, such a kit provides a LRAT detector, e.g., a detectable antibody (which may be directly labeled or which may be detected with a secondary labeled reagent).

The immunoassays discussed above involve using antibodies directed against the LRAT protein or fragments thereof. The production of such antibodies is described below.

Anti-LRAT Antibodies

Such antibodies include but are not limited to polyclonal, monoclonal, chimeric, single chain, Fab fragments, and Fab expression library.

Various procedures known in the art may be used for the production of polyclonal antibodies to LRAT polypeptides or derivative or analog thereof. For the production of antibody, various host animals can be immunized by injection with the antigenic polypeptide, including but not limited to rabbits, mice, rats, sheep, goats, etc.

For preparation of monoclonal antibodies directed toward the LRAT polypeptides, any technique that provides for the production of antibody molecules by continuous cell lines in culture may be used. These include but are not limited to the hybridoma technique originally developed by Kohler and Milstein (Nature 1975, 256:495–497), as well as the trioma technique, the human B-cell hybridoma technique (Kozbor et al., Immunology Today 1983, 4:72; Cote et al., Proc. Natl. Acad. Sci. USA 1983, 80:2026–2030), and the EBV-hybridoma technique to produce human monoclonal antibodies (Cole et al., In *Monoclonal Antibodies and Cancer Therapy,* 1985, Alan R. Liss, Inc., pp. 77–96). In an additional embodiment of the invention, monoclonal antibodies can be produced in germ-free animals (PCT Publication No. WO 89/12690).

According to the invention, techniques described for the production of single chain antibodies (U.S. Pat. Nos. 5,476, 786; 5,132,405; and 4,946,778) can be adapted to produce the LRAT polypeptide-specific single chain antibodies. Indeed, these genes can be delivered for expression in vivo. An additional embodiment of the invention utilizes the techniques described for the construction of Fab expression libraries (Huse et al., Science 1989, 246:1275–1281) to allow rapid and easy identification of monoclonal Fab fragments with the desired specificity for a LRAT polypeptide, or its derivatives, or analogs.

Antibody fragments which contain the idiotype of the antibody molecule can be generated by known techniques.

For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In Vivo Diagnostics

The direct assays of LRAT expression or activity may be preferably performed in vitro, since LRAT expression will typically be determined in cells extracted from a subject, e.g., by biopsy or tumor resection.

Alternatively, and especially when the targeted protein or mRNA cannot be easily detected by collecting a biological sample such as with lung and ovarian cancer, in vivo diagnostic method can then be contemplated. In vivo diagnostics may involve the use of any technique well-known by one skilled in the art.

In vivo diagnostics especially refers to in vivo imaging methods, which permit the detection of a labeled probe or antibody that specifically hybridize or bind mRNA or protein, respectively, in the subject's body. Such methods include magnetic resonance spectroscopy, positron-emission tomography (PET) and single photon emission tomography (SPECT). For purposes of in vivo imaging, the type of detection instrument available is a major factor in selecting a given label. For instance, radioactive isotopes and paramagnetic isotopes are particularly suitable for in vivo imaging. The type of instrument used will guide the selection of the radionuclide. For instance, the radionuclide chosen must have a type of decay which is detectable for a given type of instrument. However, any conventional method for visualizing diagnostic imaging can be utilized in accordance with this invention. In one embodiment, a radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable as radioactive isotopes are $^{99}$mTc, $^{123}$I, $^{131}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl. Examples of paramagnetic isotopes, particularly useful in Magnetic Resonance Imaging ("MRI"), include $^{157}$Gd, $^{55}$Mn, $^{162}$Dy, $^{52}$Cr, and $^{56}$Fe.

Therapeutic Applications

The present invention further provides a method for the prevention or treatment of carcinoma, which method comprises increasing LRAT expression or activity in a subject or patient.

A "subject" or "patient" is a human or an animal likely to develop carcinoma, more particularly a mammal, preferably a rodent or a primate, and most preferably a human, as described above in connection with diagnostic applications.

The term "prevention" refers to the prevention of the onset of the disease, which means to prophylactically interfere with a pathological mechanism that results in the disease. In the context of the present invention, such a pathological mechanism can be a decrease of LRAT expression. The patient may be a subject that has an increased risk of developing the disease.

The term "treatment" means to therapeutically intervene in the development of a disease in a subject showing a symptom of this disease. In the context of the present invention, these symptoms can include development of hyperplasia, tumors, and tumor metastasises.

The term "therapeutically effective amount" is used herein to mean an amount or dose sufficient to increase the level of LRAT activity, e.g., to about 10 percent, preferably by about 50 percent, and more preferably by about 90 percent of the level found in normal epithelial cells. Preferably, a therapeutically effective amount can ameliorate or present a clinically significant deficit in the activity, function and response of the subject. Alternatively, a therapeutically effective amount is sufficient to cause an improvement in a clinically significant condition in the host.

The substance that increases LRAT activity is advantageously formulated in a pharmaceutical composition, with a pharmaceutically acceptable carrier. This substance may be then called active ingredient or therapeutic agent against LRAT.

The concentration or amount of the active ingredient depends on the desired dosage and administration regimen, as discussed below. Suitable dose ranges may include from about 1 mg/kg to about 100 mg/kg of body weight per day.

The pharmaceutical compositions may also include other biologically active compounds.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

According to the invention, the pharmaceutical composition of the invention can be introduced parenterally, transmucosally, e.g., orally (per os), nasally, or rectally, or transdermally. Parental routes include intravenous, intra-arteriole, intramuscular, intradermal, subcutaneous, intraperitoneal, intraventricular, and intracranial administration. Preferably, the therapeutic composition is introduced intratumorally, i.e., by direct injection in the tumor.

In a preferred embodiment, vectors comprising a sequence encoding LRAT may be administered by any known methods, such as the methods for gene therapy available in the art. Exemplary methods are described below. For general reviews of the methods of gene therapy, see, Goldspiel et al., Clinical Pharmacy 1993, 12:488–505; Wu and Wu, Biotherapy 1991, 3:87–95; Tolstoshev, Ann. Rev. Pharmacol. Toxicol. 1993, 32:573–596; Mulligan, Science 1993, 260:926–932; and Morgan and Anderson, Ann. Rev. Biochem. 1993, 62:191–217; May, TIBTECH 1993, 11:155–215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA 1989, 86:8932–8935; Zijlstra et al., Nature 1989, 342:435–438).

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-β-1-4-N-acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem. 1987, 62:4429–4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., Mol. Therapy 2000, 2:339–47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188).

Vectors in vitro, in vivo, and ex vivo include viral vectors, such as lentiviruses, retroviruses, herpes viruses, adenoviruses, adeno-associated viruses, alpha-viruses (particularly Sindbis virus), vaccinia viruses, baculoviruses, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication WO 95/28494.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 1992, 7:980–990). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

The gene can be introduced in a retroviral vector, e.g., as described in Anderson et al., U.S. Pat. No. 5,399,346; Mann et al., Cell 1983, 33:153; U.S. Pat. Nos. 4,650,764, 4,980,289, and 5,124,263; Markowitz et al., J. Virol. 1988, 62:1120; Temin et al., U.S. Pat. No. ; EP 453242, EP178220; Bernstein et al, Genet. Eng. 1985, 7:235; McCormick, Bio Technology 1985, 3:689; PCT; and Kuo et al. 1993, Blood 82:845. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (PCT Publication No. WO 90/02806) and the GP+envAm-12 cell line (PCT Publication No. WO 89/07150). Retrovirus vectors can also be introduced by DNA viruses, which permits one cycle of retroviral replication and amplifies tranfection efficiency (see PCT Publication Nos. WO 95/22617, WO 95/26411, WO 96/39036, WO 97/19182).

In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest (see, Naldini, Curr. Opin. Biotechnol. 9:457–63, 1998; see also Zufferey, et al., J. Virol. 72:9873–80, 1998; Kafri, et al., J. Virol. 73: 576–584, 1999).

Gene transduction based on alphavirus, particularly Sindbis virus, has been well-studied in vitro (see Straus et al., Microbiol. Rev. 1994, 58:491–562; Altman-Hamamdzic et al., Gene Ther. 1997, 4:815–822; Gwag et al. Mole. Brain Research. 1998, 63:53–61; Bredenbeek et al., J Virol 1993, 67:6439–6446; Liljestrom et al., Biotechnology 1991, 9:1356–1361; Piper et al., *Meth. Cell Biol.* 1994,43:55–78; and Grusby et al., Proc Natl. Acad. Sci. USA 1993, 90:3913–3917) and there are several reports of in vivo Sindbis virus gene transfer to the central nervous system (Duncan et al., J Gen Virol. 1978, 40:45–61; Alemany et al., J Gen Virol. 2000, 81 Pt 11:2605–2609; and Alemany et al., Nat Biotechnol. 2000, 18:723–727) as well as to to antigen presenting cells (see Tsuji et al., J Virol 1998, 72:6907–6910; Hariharan et al., J Virol 1998, 72:950–958; Pugachev et al., Virology 1995, 212:587–594; and Xiong et al., Science 1989, 243:1188–1191).

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320–330), defective herpes virus vector lacking a glyco-protein L gene (Patent Publication RD 371005 A), or other defective herpes virus vectors (PCT Publication Nos. WO 94/21807 and WO 92/05263); an attenuated adenovirus vector, such as the vector described by Stratford-Perricaudet et al. (J. Clin. Invest. 1992, 90:626–630; see also La Salle et al., Science 1993, 259:988–990); various replication defective adenovirus and minimum adenovirus vectors have been described in PCT Publication Nos. WO 94/26914, WO 95/02697, WO 94/28938, WO 94/28152, WO 94/12649, WO 95/02697, and WO 96/22378); and a defective adeno-associated virus vector (Samulski et al., J. Virol. 1987, 61:3096–3101; Samulski et al., J. Virol. 1989, 63:3822–3828; Lebkowski et al., Mol. Cell. Biol. 1988, 8:3988–3996; PCT Publication Nos. WO 91/18088 and WO 93/09239; U.S. Pat. Nos. 4,797,368 and 5,139,941; European Publication No. EP 488 528).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), Transgene (Strasbourg, France; adenoviral, vaccinia, retroviral, and lentiviral vectors), and Vector Therapeutics (New York; Sindbis vectors).

In another embodiment, the vector can be non-viral. Such vectors include "naked" DNA, and transfection facilitating agents (peptides, polymers, etc.). Synthetic cationic lipids can be used to prepare liposomes for transfection of a gene encoding (Felgner, et. al., Proc. Natl. Acad. Sci. U.S.A. 1987, 84:7413–7417; Felgner and Ringold, Science 1989, 337:387–388, see Mackey, et al., Proc. Natl. Acad. Sci. USA 1988, 85:8027–8031; Ulmer et al., Science 1993, 259:1745–1748). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 1992, 267:963–967; Wu and Wu, J. Biol. Chem. 1988, 263:14621–14624; Hartmut et al., Canadian Patent Application No. 2,012,311, filed Mar. 15, 1990; Williams et al., Proc. Natl. Acad. Sci. USA 1991, 88:2726–2730). Receptor-mediated DNA delivery approaches can also be used (Curiel et al., Hum. Gene Ther. 1992, 3:147–154; Wu and Wu, J. Biol. Chem. 1987, 262:4429–4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C. P. Acad. Sci., 321:893, 1998; WO 99/01157; WO 99/01158; WO 99/01175).

EXAMPLES

The invention is illustrated in the following working examples, which are provided by way of illustration and are not intended to be limiting.

Example 1

Reduced Expression of LRAT in Oral, Skin and Breast Carcinoma Cells

This Example reports the analysis of retinol metabolism in several types of cultured normal human cell types such as fibroblasts, endothelial cells and various types of epithelial cells. Normal epithelial cells, but not fibroblasts and endothelial cells, esterify large amounts of retinol. We also show that these retinyl esters can be hydrolyzed in the normal epithelial cells to retinol, retinoic acid, and other retinol metabolites over a time course of approximately six to eight days. In contrast, cultured human carcinoma cells esterify very little or no retinol, and thus have essentially no or extremely limited retinyl ester stores. Most significantly, the lack of ability to esterify retinol in the oral cavity, skin, and breast carcinoma cell lines is correlated with a great reduction in LRAT protein levels.

Materials and Methods

Materials

Radiolabeled retinol (all-trans $^3$H -(Buck, et al. J. Exp. Med. 1993 178:675–680; Hong, et al., Retinoids in Oncology 1993, Marcel Dekker, New York) specific activity in the range of 27–47 Ci/mmol) was purchased from New England Nuclear/Dupont (Boston, Mass.). All other chemicals used, unless specified, were purchased from Sigma Chemical Co. (St. Louis, Mo.).

Cells and Culture Conditions

The origins and properties of the cell strains used have been described previously (Guo et al., Cancer Res. 1998, 58:66–176; Chen et al., Cancer Res. 1997, 57:4642–4651; Hu, L. et al. Cancer Res. 1991, 51:3972–3981; Crowe, et al. Differentiation 1991, 48:199–208 and see Table 1). The fibroblast cell strains CCD42-SK and GM0970 were obtained from the American Type Culture Collection (Rockville, Md.). The normal human umbilical vein endothelial cells (HUVEC), normal human bronchial epithelial cells (NHBE), normal human mammary epithelial cells (HMEC), and normal human epidermal keratinocytes (NHEK) were from Clonetics Corp. (Walkersville, Md.). The ADO74 and 184B5 lines were from Dr. M. Stampfer. For maintenance of the cell strains, the NT2 human teratocarcinoma line was cultured in DME plus 10% fetal bovine serum; OKF4, OKP-7, and SCC-25 were cultured in keratinocyte serum-free medium (Life Technologies, Grand Island, N.Y.) according to the manufacturer's guide; SCC-40 cells were maintained in a consensus medium consisting of a mixture of Dulbecco's modified Eagle medium and Ham's F12 medium (1:1) supplemented with 5% fetal calf serum (FCS), 0.4 µg/ml hydrocortisone, 10 µg/ml epidermal growth factor, and 5 µg/ml insulin. MCF-7 and MDA-MB-231 were cultured in DME plus 10% FCS and 5 µg/ml insulin. ADO74 cells (Stampfer, et al. Proc. Natl. Acad. Sci. 1985, 82:2394–2398; Stampfer, et al. *Breast Cancer: Cellular and Molecular Biology.* 1988, Kluwer Academic Publishers, Boston, Mass., pp. 1–24) were cultured in MEGM (Clonetics); CCD42-SK and GM0970 were cultured in DME plus 10% FCS. The normal human endothelial cell strains, the normal human bronchial epithelial cell strains, the normal human mammary epithelial cells, and the normal human epidermal keratinocytes were cultured in endothelial growth medium (EGM), bronchial epithelial growth medium (BEGM), mammary epithelial growth medium (MEGM), and keratinocyte growth medium (KGM), respectively (Clonetics). All of the normal cell strains used for experiments were passage 8 or less. For radiolabeling, Northern, and Western analyses of all of the cell strains and lines, a consensus medium consisting of DME plus 5% fetal bovine serum was employed. The cells were switched to the consensus medium at the time of addition of the [$^3$H]retinol.

TABLE 1

Summary of Human Cell Strains and Lines

| Cell Strains Location/Origin | | Cell Type or Lesion |
|---|---|---|
| Normal Name | | |
| OKF4 | floor of mouth | typical nonkeratinizing oral mucosa |
| OKP7 | soft palate | special nonkeratinizing oral mucosa |
| ADO74 (184) | breast | epithelial |
| HMEC | breast | epithelial |
| NHEK | skin | interfollicular epidermal |
| NHBE | lung | bronchial epithelial |
| HUVEC | umbilical vein | endothelial |
| GM0970 | skin | fibroblast |
| CCD42-SK | skin | fibroblast |
| Tumor Name | | |
| SCC-25 | side of tongue/ floor of mouth | squamous cell carcinoma (SCC) |
| SCC-40 | soft palate | SCC |
| SCC-12 | facial skin | SCC |
| SCC-13 | facial skin | SCC |
| MCF-7 | pleural effusion | breast adenocarcinoma |
| MDA-MB-231 | pleural effusion | breast adenocarcinoma |
| NT2 | — | teratocarcinoma |

[$^3$H]-Retinol Radiolabeling

All retinoid solutions and samples were handled under red or dim light. Cells were plated at $1 \times 10^6$ cells per 60 mm dish 24 h prior to [$^3$H]retinol addition. Cells were washed three times with the consensus medium prior to labeling and cultured for various periods in 2 ml of labeling medium containing 50 nM [$^3$H]retinol in the consensus medium (approximately 2 µCi/ml). A separate control consisting of labeling medium without cells was included during the incubation period. Cells and one-fourth of the media were collected. Cells were washed once with 0.5 ml of phosphate-buffered saline (PBS) and removed from the monolayer in 0.5 ml PBS by scraping. Samples were stored at −70° C. until retinoid extraction. The cell numbers were counted from parallel dishes from each treatment at the time of cell harvest.

For the pulse chase experiments, the cells were cultured for 24 h in 100 nM [$^3$H]retinol. Cells were then rinsed three times with warm PBS over a 30 minute period, and then incubated in growth medium without [$^3$H]retinol for an additional one to eight days. At various times following the removal of [$^3$H]retinol from the medium, dishes of cells were harvested and retinoids were extracted and subjected to HPLC analysis.

Extraction of Retinoids and HPLC

The retinoids were extracted as described previously (McLean, et al. *Clin. Chem.* 1982, 28:693–696). Non-radiolabeled retinoid standards were added to the samples prior to extraction. Briefly, 350 µl acetonitrile/butanol (50:50, v/v), 0.1% butylated hydroxytoluene (BHT) was added to 0.5 ml of cells or medium samples. The mixtures were vortexed thoroughly for 30 sec. After addition of 300 µl of a saturated (1.3 kg/liter) $K_2HPO_4$ solution and thorough mixing, the samples were centrifuged for 10 min at 3000 g. The upper organic layer was collected and transferred to an injector vial for automated HPLC analysis.

The HPLC analysis was performed using a Waters Millenium system (Waters Corp.) to separate the various retinoids. Samples were applied to an analytical 5 µm reverse-phase $C_{18}$ column (Vydac, Hesperia, Calif.) at a flow rate of 1.5 ml/min. The gradient consisted of a 35 min linear gradient from 15 mM ammonium acetate, pH 6.5, in water to 85% acetonitrile in a 10 min linear gradient from 85% acetonitrile to acetonitrile-dichloromethane (80:20) followed by a 15 min hold. Non-radiolabeled retinoid standards were run concurrently and monitored at a wavelength of 340 nm while a Packard A-500 radiochromatography detector (Packard Instruments, Downers Grove, Ill.) was used to monitor the labeled retinoids.

Retinoids were identified by HPLC based on at least two criteria: an exact match of the retention times of unknown peaks with those of authentic retinoid standards and identical UV spectra (220–400 nm) of unknowns against spectra from authentic retinoid standards during HPLC by the use of the photodiode array detector. RA was also identified by the shift of the retention time of the methylated RA derivative to the same position as the corresponding methyl ester of the RA standard. The methyl ester of RA was synthesized by reaction with diazomethane (Randolph, et al. *J. Biol. Chem.* 1993, 268:9198–9205).

RNA Isolation and Northern Blot Analysis

Total cellular RNA was isolated from cultured cells using RNA Stat-60 according to the manufacturer's instruction (Tel-Test, Friendswood, Tex.). RNA was electrophoretically fractionated by size on 1% agarose/2.2 M formaldehyde gels, transferred to nylon filters by blotting, and attached to the filters using a UV Stratalinker 1800. The cDNA probes used in this analysis were radiolabeled with [$^{32}$P]dCTP using a random primer labeling kit (Boehringer Mannheim, Indianapolis, Ind.) according to the manufacturer's directions. Glyceraldehyde phosphate dehydrogenase cDNA was used as a probe for Northern blots as described previously (Guo, et al. Cancer Res. 1998, 58:166–176; Chen, et al. J. Biol. Chem. 1996, 271:14971–14980). AHD-2 cDNA, isolated from a murine liver cDNA library by this laboratory (Chen, Mol. Pharm. 1994, 46:88–96), was used as a probe; this cDNA encodes an aldehyde dehydrogenase class I enzyme, also called ALDH-1 in human. The human LRAT cDNA clone was an Eco RI fragment (840 bp) as described (Ruiz, et al. J. Biol. Chem. 1999, 274:3834–3841). The human neutral, bile salt independent retinyl ester hydrolase and the hepatic, bile sale dependent retinyl ester hydrolase were EST clones #g4069398 and #g2237729, respectively, from Genome Systems (St. Louis, Mo.).

Blots were prehybridized and hybridized at 42° C. in 50% (w/v) formamide/5× SSC-50 mM NaH$_2$PO$_4$, pH 7.4, 5 mM EDTA-0.08% polyvinylpyrrollidone-10% (w/v) bovine serum albumin, and 10% (w/v) salmon sperm DNA. After 10 to 16 h of hybridization, blots were washed twice in 2× SSC, 0.1% SDS for 20 min at room temperature, and twice in 0.2× SSC, 0.1% SDS at 50° C.

Western Analysis

This procedure was carried out as described previously Ruiz, et al., J. Biol. Chem. 1999, 274:3834–3841). Briefly, polyclonal antisera were generated in rabbits to a mixture of two different LRAT peptides. Total cell protein was used, and blot analysis on nitrocellulose filters was performed using antiserum diluted to $\frac{1}{1,000}$ for detection of LRAT. Protein bands were detected by the ECL system (Pierce, Rockford, Ill.).

Results

Analysis of Metabolism in Normal Cultured Human Fibroblast, Endothelial, and Epithelial Cells We examined two different normal human fibroblast cell strains, GM0970 and CCD42-SK, for their ability to metabolize [$^3$H]retinol (see Table 1 for a list of cell strains and lines analyzed). Essentially no retinol metabolism occurred in these fibroblast cell strains even over a 15–24 h period of culture in the presence of [$^3$H]retinol (FIG. 1, panel A, GM0970; CCD42-SK, data not shown). We also examined normal human umbilical vein endothelial cells (HUVEC) for their ability to metabolize [$^3$H]retinol. Again, only trace amounts of retinyl esters were found in these human umbilical vein endothelial cells even after 15 h of culture in the presence of 50 nM [$^3$H]retinol (FIG. 1, panel B).

In contrast, both normal human bronchial epithelial cells (NHBE) (FIG. 1, panel C) and normal human epidermal keratinocytes (NHEK) (FIG. 1, panel D) exhibited extensive esterification of [$^3$H]retinol to retinyl esters, with the predominant retinyl ester as retinyl oleate. The bronchial epithelial cells, after 15 h of culture in the presence of [$^3$H] retinol in the medium, also exhibited a much higher internal [$^3$H]retinol concentration than the normal human epidermal keratinocytes (FIG. 1, compare panels C and D). We observed similar levels of [$^3$H]retinol esterification in exponentially growing cultures of epithelial cells and in confluent cultures (data not shown).

Thus, we conclude that normal human epithelial cells take up and esterify a large proportion of the [$^3$H]retinol to which they are exposed in the medium, consistent with our previous data using normal human mammary epithelial cells (Chen, et al. Cancer Res. 1997, 57:4642–4651) and normal cell strains from the oral cavity and skin (Guo, et al. Cancer Res. 1998, 58:166–176). In contrast, human fibroblast strains and human umbilical vein endothelial cells do not exhibit retinol esterification under these conditions. Our data are consistent with two previous reports for cultured fibroblasts (Rundhaug, et al. Cancer Res. 1987, 47:5637–5643; Randolph, et al. J. Invest. Dermatol. 1998, 111:478–484) in which the authors demonstrated the lack of significant retinol metabolism in murine 10t1/2 cells and human dermal fibroblasts, respectively. This lack of retinol esterification in normal human dermal fibroblasts and endothelial cells may reflect a less important role for endogenous retinoids in these cell types.

Retinol Esterification in Cultured Normal Epithelial Cell Strains vs. Carcinoma Cell Lines The normal mammary epithelial cell strains HMEC and ADO74; a normal human epidermal keratinocyte cell strain, NHEK; and an oral cavity epithelial cell strain, OKP-7, were cultured for various times in the presence of [$^3$H]retinol. By approximately 6–8 h following the addition of 50 nM [$^3$H]retinol to the medium, all of the [$^3$H]retinol in the medium had been esterified by these normal epithelial cell strains. Shown here are retinoids extracted from cells 22 h after addition of [$^3$H]retinol to the culture medium (FIG. 2, except for ADO74 (Chen, et al. Cancer Res. 1997, 57:4642–4651). It can be seen that there is almost no [$^3$H]retinol in the normal epithelial cells, as all of the [$^3$H]retinol has been converted to various types of [$^3$H] retinyl esters, with [$^3$H]retinyl oleate and [$^3$H]retinyl palmitate the most prevalent (FIGS. 2A, B, C). The MCF-7 breast carcinoma cell line, in contrast, even after 22 h of culture in the presence of [$^3$H]retinol in the medium, did not exhibit [$^3$H]retinol esterification (FIG. 2E). While some [$^3$H]retinol esterification was exhibited by the SCC-12 skin squamous carcinoma line (FIG. 2F), the SCC-40 carcinoma line from the soft palate did not exhibit any significant [$^3$H]retinol esterification even after 22 h of exposure to [$^3$H]retinol in the medium (FIG. 2G). As a result, the intracellular levels of [$^3$H]retinyl esters in the tumor cell lines cultured in the presence of [$^3$H]retinol are much lower than those achieved in the normal cell strains, and much less of the total [$^3$H]retinol added to the medium is metabolized by the tumor cells (compare FIG. 2, panels E, F, G with panels A, B, and C; and FIG. 2, panels I, J for quantitation).

Figure 3B:
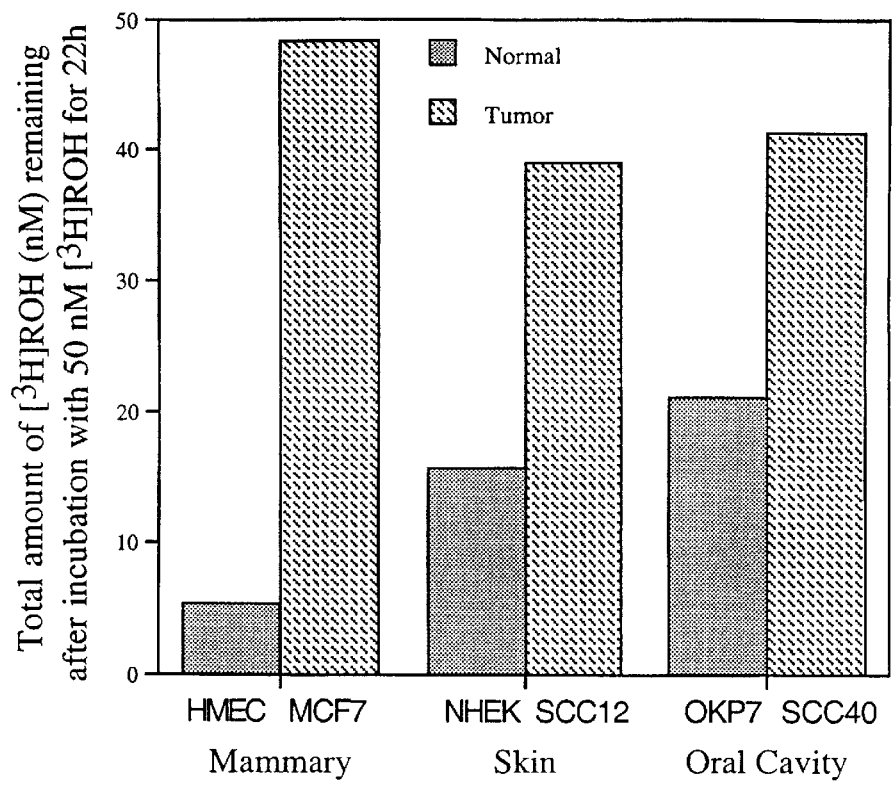

[$^3$H]Retinyl Ester Content in Normal Epithelial Cell Strains vs. Carcinoma Cell Lines Following [$^3$H]Retinol Removal From the Medium As the carcinoma cells appeared to be unable to store retinol in the ester form, we next wanted to ascertain the levels of various retinoids in these cells over time following the removal of [$^3$H]retinol from the medium. Therefore, in this series of experiments the cells were cultured in the presence of 100 nM [$^3$H]retinol and 900 nM retinol in the medium for 24 h, followed by the removal of the [$^3$H]retinol from the medium. The cells were washed several times, and then dishes of cells were harvested at various times following the removal of [$^3$H]retinol from the medium, retinoids were extracted from the cells, and the [$^3$H]retinoids were analyzed by HPLC. In the normal cell strains from the oral cavity (OKP-7) and the breast (ADO74), substantial amounts of [$^3$H]retinyl esters were present at the time of [$^3$H]retinol removal from the medium (day 0, FIG. 3). The [$^3$H]retinyl esters remained in the cells at high levels for the next four to eight days (FIG. 3, and data not shown). In addition, 1–2, $\mu$M and 3–10 $\mu$M intracellular concentrations of [$^3$H]retinoic acid and [$^3$H]retinol, respectively, were observed in the OKP-7 and ADO74 normal cell strains over this time period [(FIG. 3, panels A, B, and E (enlarged scale of internal [$^3$H]RA from panels A and B)]. Even at four days after the removal of [$^3$H]retinol from the medium, the intracellular concentration of [$^3$H]retinyl esters was approximately 26 µM in the OKP-7 cells and 30 µM in ADO74 cells.

In contrast, the SCC-40 squamous cell carcinoma line from the oral cavity and the MDA-MB-231 breast carcinoma line had no detectable retinyl esters at the time of [$^3$H]retinol removal (day 0, FIG. 3, panels C, D). The intracellular [$^3$H]retinol concentration in these cells decreased very rapidly following removal of [$^3$H]retinol from the medium, and within 24 h the SCC-40 and MDA-MB-231 cells had no detectable [$^3$H]retinol intracellularly (FIG. 3, note the difference in y axes between the graphs of retinoid levels in the normal epithelial cell strains and the carcinoma lines). Similar results were obtained for the breast carcinoma line MCF-7 (data not shown). Thus, we conclude from this experiment that the retinyl esters in the normal cell strains are slowly hydrolyzed over a period of several days to generate retinol and more bioactive retinoids such as retinoic acid in these cells. In contrast, the carcinoma lines become profoundly retinoid deficient when cultured in the absence of retinol in the medium.

Figure 4A:
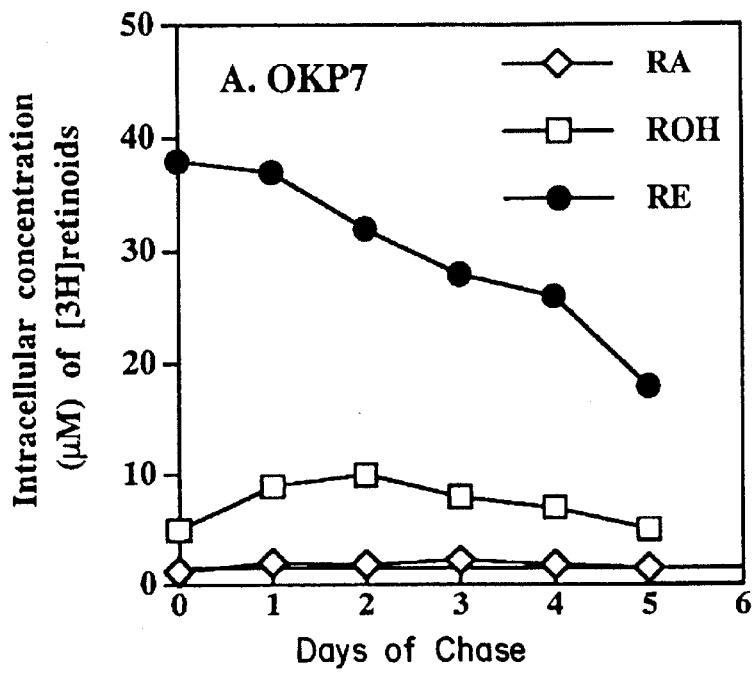
FIGS. 4A, 4B, 4C, 4D and 4E. Kinetics of [$^3$H]Retinol Metabolism in OKP-7, SCC-40, ADO74, and MDA-MB-231 Cells. The OKP-7 and ADO74 are normal human epithelial cell strains from the oral cavity and the mammary gland, respectively. SCC-40 and MDA-MB-231 are human carcinoma cell lines from the oral cavity and breast, respectively. Cells were radiolabeled with 100 nM [$^3$H]retinol plus 900 nM retinol for 24 h. Cells were then washed three times with phosphate buffered saline, and the medium was replaced with fresh growth medium (day 0). At various times thereafter, cell samples and media samples were harvested, and retinoids were extracted and separated by reverse phase HPLC analysis. Cell numbers for each cell line were determined by counting a separate dish, seeded with the same number of cells, at the time of harvest. The intracellular concentration of each of the [$^3$H]retinyl esters, [$^3$H]retinol, and [$^3$H]retinoic acid produced during the chase period after removal of the [$^3$H]retinol label at day 0 was calculated as described (Guo, et al. Cancer Res. 1998, 58:166–176; Chen, et al. Cancer Res. 1997, 57:4642–4651) and plotted (y-axis) vs. days after [$^3$H]retinol removal (x-axis). This experiment was performed two times, with very similar results. Data from one experiment are shown here. Note the differences in the y axes between the normal cell strains and the carcinoma lines. A) OKP-7; B) ADO74; C) SCC-40; D) MDA-MB-231; E) [$^3$H]RA, internal levels from panels A, B, C, and D; more sensitive scale. ROH, retinol; RE, retinyl esters.
Figure 4B:
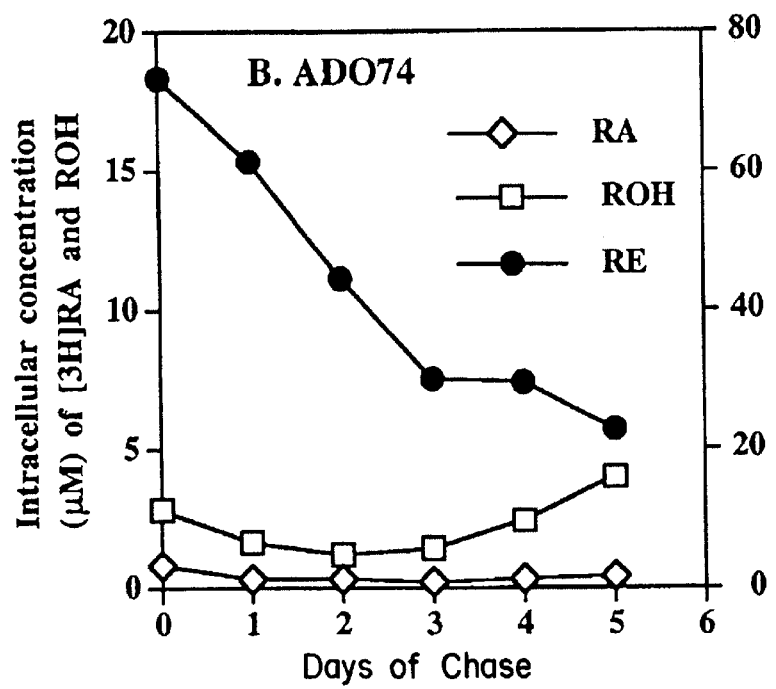

Expression of Genes Encoding Enzymes Involved in Retinol Metabolism in Cultured Normal Human Epithelial, Endothelial, and Fibroblast Cells We next examined the normal human cell strains for expression of genes for various enzymes involved in the metabolism of retinol, including genes encoding enzymes involved in the conversion of retinol to retinoic acid and the gene encoding LRAT. For these experiments cells were cultured either in the presence or absence of nonradiolabeled, 1 µM retinoic acid for 48 h, followed by cell harvesting and RNA isolation. The normal human umbilical vein endothelial cells (HUVEC) and the normal fibroblast strains CCD42-SK and GM0970 do not express detectable levels of LRAT transcripts (FIG. 4A). The normal human mammary cell strain (HMEC) and the normal human bronchial epithelial cells (HNBE) exhibited expression of both the 5 kb and 2.5 kb LRAT transcripts (FIG. 4B). The human NT2 teratocarcinoma cell line, which esterifies large amounts of retinol (Guo and Gudas, unpublished), also expresses high levels of the 5 kb and 2.5 kb LRAT transcripts (FIGS. 4A, B). Thus, the levels of LRAT mRNA expression correlate with the abilities of these various normal cell types to esterify retinol, as shown in FIGS. 1 and 2. Culture in the presence of retinoic acid for 48 h did not greatly influence the levels of LRAT mRNA in these cells; a slight increase in LRAT mRNA was noted following RA addition.

With the exception of the human endothelial cells, none of these various human cell strains, when cultured in the presence or absence of retinoic acid, expressed detectable levels of AHD-2 mRNA; however, mouse liver cells expressed a high level of AHD-2 message as a positive control (data not shown). AHD-2, which is called ALDH-1 in humans, can utilize retinaldehyde as a substrate, converting it to RA. The RA hydroxylase (CYP26) gene was not expressed by any of these normal cell strains at detectable levels (data not shown).

Figure 4C:
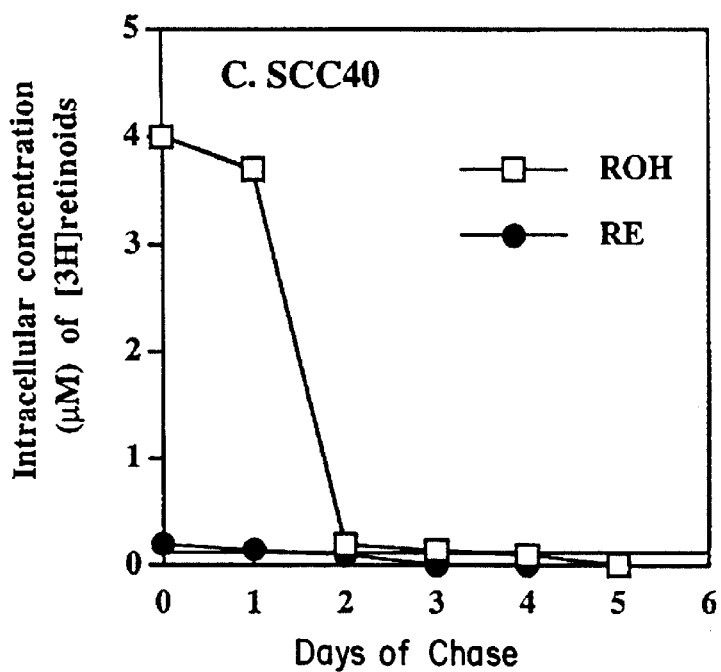
Figure 4D:
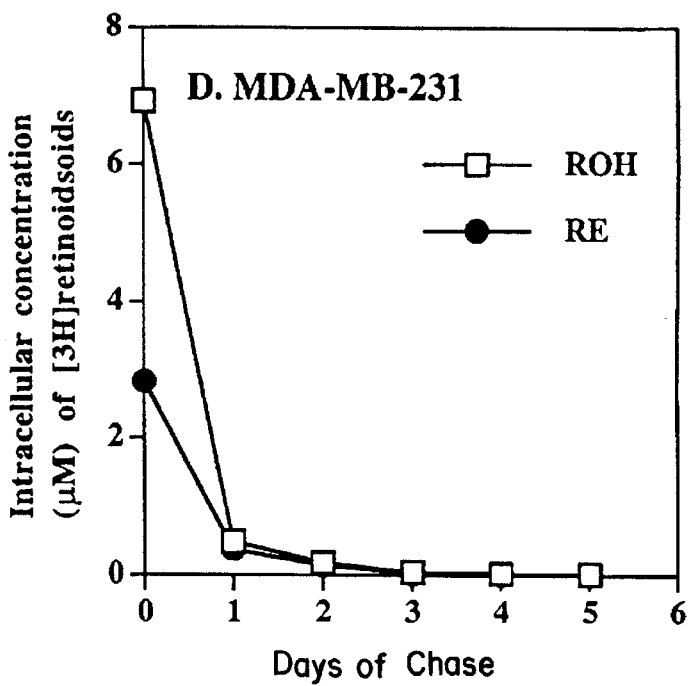
Figure 4E:
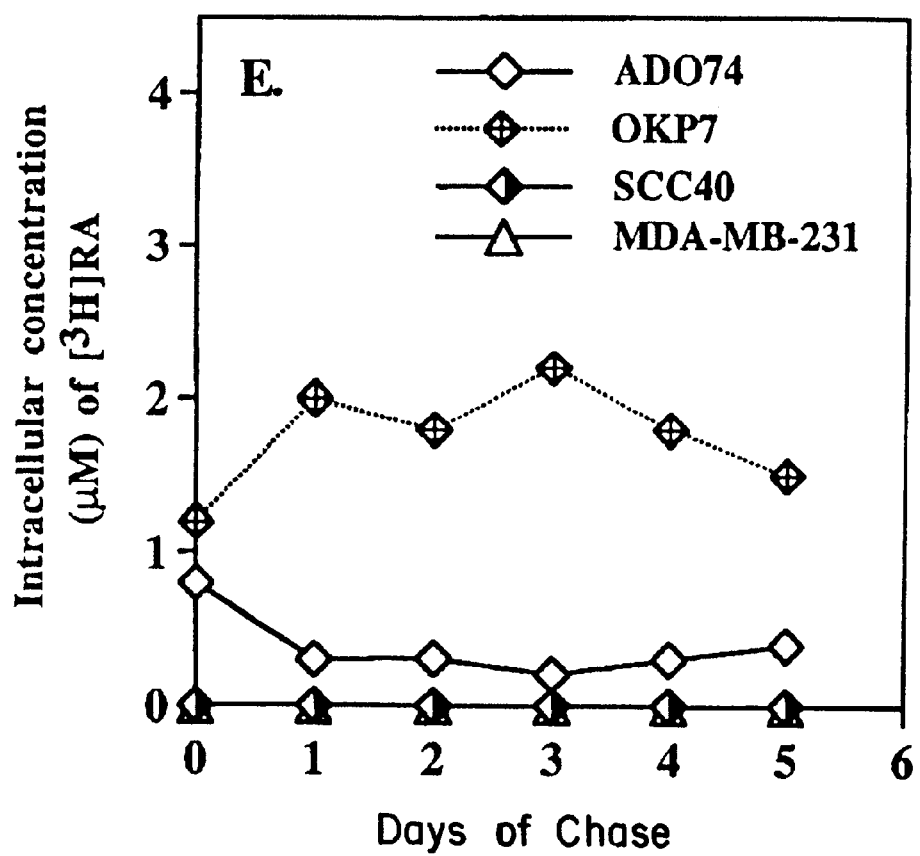

A Comparison between Normal and Tumor Cell Lines of the Expression of Genes Encoding Enzymes for Retinol Metabolism In the next series of experiments, the expression of LRAT mRNA was examined in a normal cell strain vs. two carcinoma lines (FIG. 4C). The normal mammary epithelial cell strain ADO74 expressed two major LRAT transcripts at 5 kb and 2.5 kb (see bold lines, FIG. 4C). MDA-MB-231 and MCF-7, estrogen receptor negative and estrogen receptor positive breast cancer lines, respectively, did not express detectable levels of LRAT transcripts at 5 and 2.5 kb. However, these tumor lines exhibited transcripts at approximately 3 and 1.5 kb (narrower lines, FIG. 4C). These aberrantly sized transcripts may reflect the use of alternative polyadenylation sequences in the tumor cells, alternative transcription start sites, or alternative splicing. In summary, the expression of the 5.0 and 2.5 kb LRAT transcripts by the normal epithelial cells correlates well with the ability of the cells to esterify retinol.

The AHD-2 gene was not expressed at detectable levels in the cultured normal human cell strain or tumor cell lines shown in FIG. 4C (data not shown). We also could not detect expression of transcripts for the two types of retinyl ester hydrolase genes, the bile salt dependent REH gene and the bile salt independent REH gene, in the normal cell strain ADO74 and in the tumor lines (data not shown). The RA hydroxylase (CYP26) gene was strongly expressed by the MCF-7 cell line following retinoic acid addition, but was not expressed at detectable levels by other tumor lines or normal cell strains cultured with or without RA (data not shown). Thus, there was no correlation of the expression of these enzymes with the tumor cell phenotype.

Analysis of LRAT Protein Levels in Normal Cell Strains and Carcinoma Cell Lines

Figure 5A:
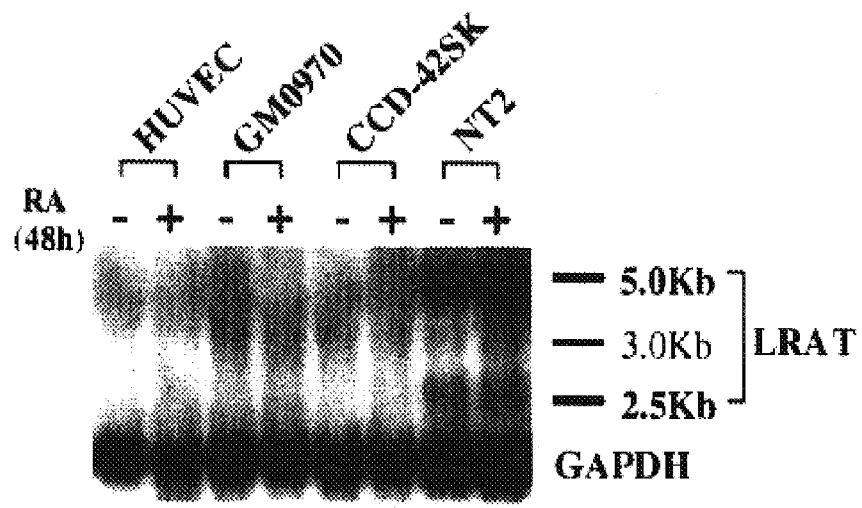
FIGS. 5A, 5B and 5C. Northern Blot Analysis of LRAT Transcripts in Cultured Normal Cell Strains and Cultured Normal Epithelial Cell Strains vs. Cultured Carcinoma Cell Lines. Cells were cultured as described in Materials and Methods, either in the presence or absence 1 mM retinoic acid for 48 h (+indicates culture in RA). RNA was isolated from the cells and Northern blot analysis was performed. Total RNA (10 mg) was loaded in each lane. Autoradiograms of blots hybridized to [$32^P$]radiolabeled cDNA probes are shown. These experiments were performed three times with very similar results; one experiment is shown. Panel A. Cell lines CCD-42SK, GM0970, HUVEC, and NT2 are described in Table 1. Panel B. Cell strains NT-2, HMEC, and HNBE are described in Table 1. Panel C. Cell lines ADO74, MCF-7, and MDA-MB-231 are described in Table 1. Top, human LRAT cDNA probe; bottom, GAPDH cDNA probe for a loading control. Transcripts of 5 and 2.5 kb, larger bold lines; transcripts of 3.0 and 1.5 kb, smaller lines. The exposure times for LRAT (2 days) and GAPDH (12 h) were the same for all of the lanes.
Figure 5B:
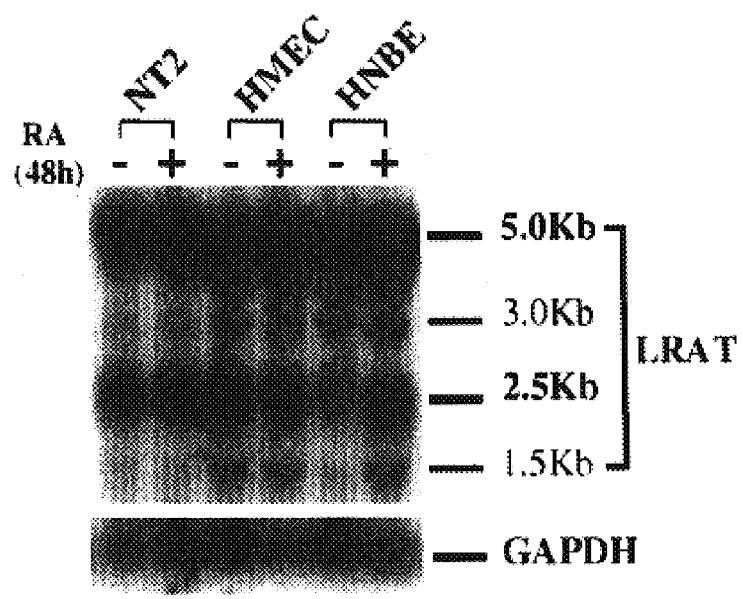
Figure 5C:
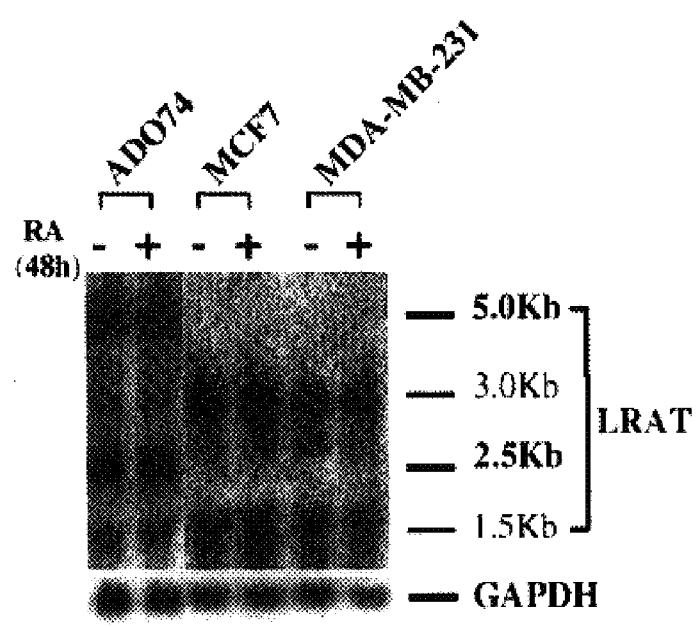
Figure 6:
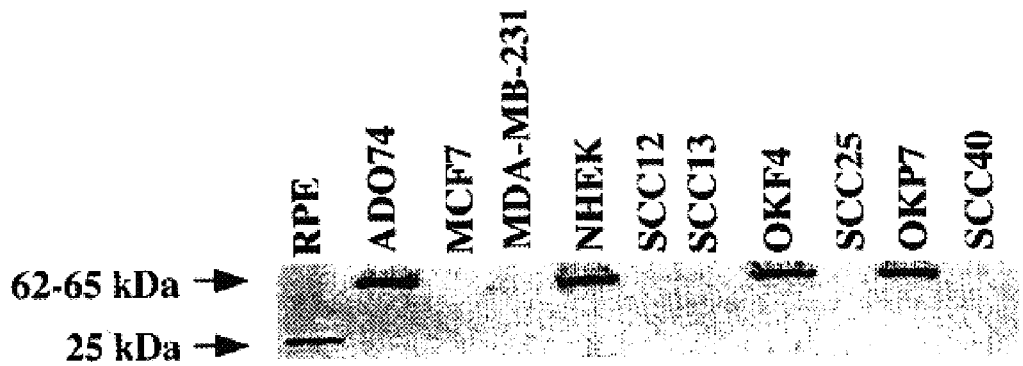
FIG. 6. Western Blot Analysis of Human LRAT Protein. 10 mg of microsomal protein from tissues or 10 mg of whole cell lysate from cultured cells was loaded in each lane. Lane 1, retinal pigment epithelial cells; lane 2, ADO74; lane 3, MCF-7; lane 4, MDA-MB-231; lane 5, NHEK; lane 6, SCC-12; lane 7, SCC-13; lane 8, OKF4; lane 9, SCC-25; lane 10, OKP7; lane 11, SCC-40 (see Table 1 for description of lines). A rabbit polyclonal antiserum against a mixture of two LRAT peptides was used for the detection; the antiserum was used at a 1:1000 dilution. Molecular weight markers in kilodaltons are indicated on the left. This experiment was performed three times with similar results. One experiment is shown here.

In all of the normal human epithelial cell strains from the breast, skin, and the oral cavity, cultured in the consensus medium, an intense protein doublet of 62–65 kD was detected which was reactive with the LRAT antibody (FIG. 5); the levels of these proteins did not change when the cells were first cultured for 48 h in the presence of 1 µM exogenous RA and then harvested for Western analysis (data not shown). In contrast, the oral cavity, skin, and mammary carcinoma lines exhibited essentially no protein which reacted with the LRAT antibodies (FIG. 5). Since small amounts of [$^3$H]retinyl esters can be seen in SCC-12 cells (FIG. 2), either ARAT or another enzyme carries out esterification in these cells or a very small amount of LRAT protein, undetectable in this Western assay, is present in the SCC-12 cells. However, the major conclusion from this data is that the normal epithelial cell strains contain much higher levels of LRAT protein than the carcinoma lines (FIG. 5). In human RPE (FIG. 5), a protein band of 25–26 kD was observed by Western analysis, using polyclonal antisera generated against a mixture of two LRAT peptides (Ruiz, et al., J. Biol. Chem. 1999, 274:3834–3841).

Discussion

We have previously demonstrated that human carcinoma cell lines exhibited a greatly reduced ability to metabolize [$^3$H]retinol to [$^3$H]retinyl esters, relative to normal human cell strains (Guo, et al. Cancer Res. 1998, 58:166–176; Chen, et al. Cancer Res. 1997, 57:4642–4651). In this report, we extend these experiments to the analysis of the expression levels of one of the enzymes involved in retinol esterification, LRAT. We previously demonstrated that ARAT enzyme activity was lower in the microsomes from the carcinoma cells vs. the normal epithelial cells (Guo et al. supra). Under the conditions of our prior assays Guo et al. supra), we were primarily detecting ARAT enzyme activity and not LRAT enzyme activity in the microsomal protein extracts from the normal cell strains vs. the tumor cell lines. In this report, we demonstrate that LRAT protein levels are low in the carcinoma cell lines as compared to the normal epithelial cell strains (FIG. 5). Since the ARAT gene has not been cloned, we do not know if ARAT mRNA and protein levels are lower in the tumor cells, though we would predict that this is the case.

We show that even though the carcinoma cells contain some [³H]retinol when cultured in the presence of [³H] retinol, as soon as the medium is changed and the [³H]retinol is removed the carcinoma cells essentially exhibit no detectable internal [³H]retinyl ester stores or internal [³H]retinol (FIG. 3). The lack of retinyl esters in the tumor cells most likely results from the low level of LRAT protein in the carcinoma cells as compared to the normal cell strains (FIG. 5).

We found that the transcripts for the neutral bile salt-independent retinyl ester hydrolase and the hepatic bile salt-dependent retinyl ester hydrolase genes are not expressed at detectable levels in the normal and tumor cell lines (data not shown). These may not be the only genes encoding enzymes involved in retinyl ester hydrolysis, or alternatively, a very low expression level may be sufficient to carry out the [³H]retinyl ester hydrolysis observed in the normal cell strains (FIG. 3).

The mechanism by which the expression of the LRAT transcripts and protein (FIGS. 4, 5) is altered in the carcinoma cells vs. the normal epithelial cells is unclear at this time. As LRAT genomic clones containing the promoter region and other potential regulatory regions are not yet available, we have not determined why the LRAT transcripts in the tumor lines are of aberrant sizes (FIG. 4B). However, we think that aberrant splicing, leading to the abnormally sized transcripts of 3 kb and 1.5 kb in the tumor cells, is the most likely explanation. These abnormally sized LRAT transcripts in the tumor cells are apparently unable to be translated into LRAT protein, since the tumor lines did not exhibit any detectable LRAT protein by Western analysis whereas the normal cell strains exhibited a high level of LRAT protein doublet at a molecular mass of 62–65 kD (FIG. 5).

It was previously shown that a major LRAT transcript of 5 kb was present in several tissues (Ruiz, et al J. Biol. Chem. 1999, 274:3834–3841), consistent with our data for the sizes of the LRAT transcripts in normal epithelial cells (FIG. 4). However, it was surprising to see that the mass of the LRAT protein, as revealed by Western blot analysis, varies among normal tissues (FIG. 5). We have performed RT-PCR analysis of the mRNA from ADO74, a normal human mammary epithelial cell strain, and have determined that the putative coding sequence (data not shown) is identical to the entire open reading frame from RPE and thus most likely contains the peptide sequences against which the antibodies are directed (Ruiz, supra). However, we have preliminary data that the open reading frame continues 5' in LRAT from the ADO74 cells (Guo, supra unpublished). Therefore, although we do not yet know the mechanism(s) whereby the larger protein species arise in some tissues (multiple transcription start sites plus alternative splicing, etc.), we are confident that the antibodies are LRAT-specific.

The functions of many retinol metabolites, including the different esters of retinol, are not fully understood. While data in the literature suggest that retinyl esters play an important role in retinol storage in various cell types in the body (for review, Blomhoff, et al. Science 1990, 250:399–404), further analysis of the actions of retinyl esters will require methods for altering retinyl ester formation from retinol in cells to assess some of the consequences in terms of cell growth and differentiation. Our data indicating that the carcinoma lines exhibit a much lower level of metabolism of [³H]retinol to [³H]retinyl esters than the normal cell strains may have important clinical implications. Cultured tumor cell lines and biopsies taken directly from patients (Hu, et al. Cancer Res. 1991, 51:3972–3981; Lotan, et al. N. Engl. J. Med. 1995, 332:1405–1410; Xu et al. Cancer Res. 1994, 54:3580–3587; Zhang et al. Cancer Res. 1994, 54:5663–5669; Houle, et al. Proc. Natl. Acad. Sci. 1993, 90:985–989; Swisshelm et al. Cell Growth Diff. 1994, 5:133–141; Seewaldt, et al. Cell Growth Diff. 1995, 6:1077–1088; Xu, et al. Cancer Res. 1997, 57:4992–4996; Khuri, et al. J. Nat. Cancer Inst. 1997, 83:199–211; Lotan, et al. J. Clin. Oncol. 2000, 18:116–121) exhibit low or undetectable levels of the message for RARβ, one of the retinoic acid receptor genes and a gene that is retinoic acid inducible in many cell types; RARβ has been implicated as a biomarker reflecting the content of active retinoids in the cells. We suggest that RARβ mRNA levels are low in the carcinoma cells in part because of their deficiency in retinyl ester stores relative to normal epithelial cells. The impairment in the ability to convert retinol to retinyl esters in the tumor cells could lead to their inappropriate growth and to the loss of normal differentiation responses because of the lack of a sufficient amount of internal retinol, stored as retinyl esters. With respect to cancer therapy, if the decrease in LRAT mRNA and protein levels results from an oncogene-associated inhibition of gene transcription, it is possible that drugs can be developed which will prevent this inhibition of LRAT transcription. If the low level of LRAT protein in carcinoma lines results from the aberrant splicing of the LRAT gene in the tumor cells, this may be more difficult to correct. An alternative therapy may involve the delivery of retinyl esters directly into the tumor cells, since this may result in higher internal levels of retinoids than those achieved by giving more retinol to the cells.

One of the most striking observations is that all of the carcinoma cell lines examined thus far exhibit an undetectable level of LRAT protein by Western analysis, as compared to all of the normal epithelial cell strains examined. We have now examined normal human epithelial cell strains and carcinoma lines from the oral cavity, breast, and skin. Our results strongly indicate that this major reduction in LRAT protein is a common feature of human carcinoma cells. Therefore, the loss of LRAT protein could potentially be used as a marker for carcinoma cells. We are currently in the process of examining biopsies of tumors taken directly from patients to assess the levels of LRAT protein in the tumor samples. It will also be important to determine at what point during the process of carcinogenesis the LRAT protein levels decline.

Example 2

Reduced Expression of LRAT in Additional Carcinoma Cells

Western Blot analysis was carried out using the procedure described above on 11 cell types. 10 μg of microsomal protein from tissues or 10 μg of whole cell lysate was loaded in each lane. The results are shown in FIG. 5 of Appendix A for cell lines as follows: Lane 1, retinol pigment epithelial cells (human RPE); lane 2, ADO 74; lane 3, MCF-7; lane 4, MDA-MB-231; lane 5, NHEK; lane 6, SCC-12; lane 7, SCC-13; lane 8, OKF-4; lane 9, SCC-25; lane 10, OKP7; lane 11, SCC-40. The cells lines are described in Table 1 of Appendix 5. In said FIG. 5, molecular weight markers in kilodaltons are indicated on the left. The experiment was performed three times with similar results. The results of one experiment are shown in said FIG. 5. As shown in said FIG. 5, in all of the normal epithelial cell strains from breast, skin and the oral cavity, cultured in the consensus medium, an intense protein doublet of 62–65 kD was detected which was reactive with LRAT antibody. In human RPE, a protein band of 25–26 kD was observed. The human RPE have a smaller form of the same LRAT protein with the same enzyme activity. The oral cavity, skin and mammary carcinoma lines exhibited essentially no protein which reacted with LRAT antibodies. All the carcinoma cells lines examined exhibited an undetectable level of LRAT protein by Western Blot analysis.

Figure 7A:
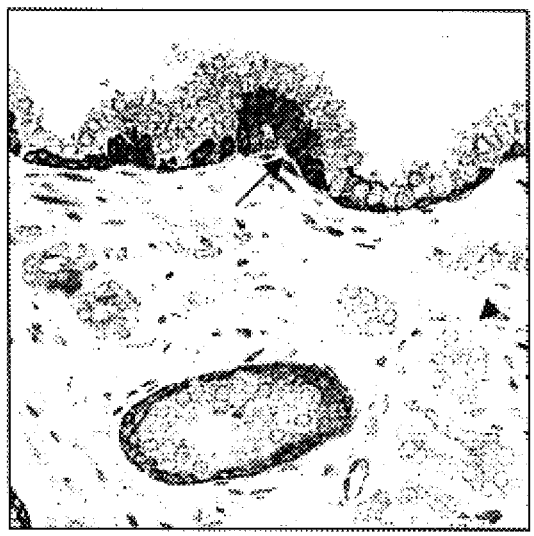
FIGS. 7A and 7B hereto show immunohistochemistry assay results for LRAT expression on a section from a prostatectomy at 200× (FIG. 1A) and 400× (FIG. 1B) which contained both normal and tumor cells.
Figure 7B:

Immunohistochemistry analysis was carried out by the procedure described above on a section from a radical prostatectomy containing both normal and tumor cells. The results are shown in FIG. 7. The same section is shown in FIG. 7A (200×) and FIG. 7B (400×). LRAT expression was localized to the basal layer of normal prostate epithelium (arrow) and expression is also seen in the luminal layer (FIG. 1B, top left). No expression was detected in adjacent tumor (arrowhead).

Several different human prostate and renal tumor samples were compared in respect to LRAT expression to benign hypertrophy (precancer) samples and normal prostate or renal epithelial cells. LRAT expression was not seen using LRAT antibody in immunohistochemistry studies of tumor. However, abundant LRAT expression was detected in normal epithelia, and intermediate levels of LRAT expression was detected in benign hypertrophy samples.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for determining the presence of cancer in epithelial cells, which method comprises determining a level of expression of active lecithin:retinol acyltransferase (LRAT) in epithelial cell from body tissue or fluid, wherein a failure to detect active LRAT expression indicates that the epithelial cells are cancerous and wherein active LRAT catalyzes esterification of retinols.

2. The method according to claim 1, wherein the level of expression of LRAT is determined by detecting a level of retinol esterification.

3. The method according to claim 2, wherein the detection of LRAT activity comprises detecting the level of esterification of retinyl esters by isolated cells.

4. The method according to claim 1, wherein the failure to detect active LRAT expression comprises a failure to detect 5.0 and 2.5 kb LRAT mRNA transcripts.

5. The method according to claim 1, wherein the level of expression of LRAT is determined by detecting LRAT protein.

6. The method of claim 5 where the detecting is by Western Blot analysis.

7. The method of claim 5 where the detecting is by immunohistochemistry.

8. The method of claim 1 where the epithelial cells are colon cells.

9. The method of claim 1 where the epithelial cells are renal cells.

10. The method of claim 1 where the epithelial cells are prostate cells.

11. The method of claim 1 where the epithelial cells are oral cavity cells.

12. The method of claim 1 where the epithelial cells are from lung.

13. The method of claim 1 where the epithelial cells are from breast.

14. The method of claim 1 where the epithelial cells are from skin.

* * * * *